United States Patent
Yaniv et al.

(10) Patent No.: US 9,617,331 B2
(45) Date of Patent: Apr. 11, 2017

(54) METHODS OF REGULATING ANGIOGENESIS BY ADMINISTERING AGENTS WHICH INCREASE APOB-100 POLYPEPTIDE

(71) Applicant: Yeda Research and Development Co. Ltd., Rehovot (IL)

(72) Inventors: Karina Yaniv, Rehovot (IL); Inbal Avraham-Davidi, Rehovot (IL); Yogev Sela, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 47 days.

(21) Appl. No.: 14/360,678

(22) PCT Filed: Nov. 27, 2012

(86) PCT No.: PCT/IL2012/050480
§ 371 (c)(1),
(2) Date: May 27, 2014

(87) PCT Pub. No.: WO2013/076730
PCT Pub. Date: May 30, 2013

(65) Prior Publication Data
US 2014/0322241 A1    Oct. 30, 2014

Related U.S. Application Data

(60) Provisional application No. 61/643,429, filed on May 7, 2012, provisional application No. 61/563,783, filed on Nov. 27, 2011.

(51) Int. Cl.
| | | |
|---|---|---|
| *A61K 38/17* | (2006.01) | |
| *A61P 35/00* | (2006.01) | |
| *A61P 35/04* | (2006.01) | |
| *C07K 14/775* | (2006.01) | |
| *C07K 16/18* | (2006.01) | |
| *C12N 15/113* | (2010.01) | |
| *C12Q 1/68* | (2006.01) | |
| *G01N 33/574* | (2006.01) | |

(52) U.S. Cl.
CPC .......... *C07K 16/18* (2013.01); *A61K 38/1709* (2013.01); *C07K 14/775* (2013.01); *C12N 15/113* (2013.01); *C12Q 1/6886* (2013.01); *G01N 33/57488* (2013.01); *C12N 2310/11* (2013.01); *C12N 2310/12* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 2003/0105003 A1* | 6/2003 | Nilsson et al. | 514/12 |
| 2005/0222029 A1 | 10/2005 | Bartel et al. | |
| 2010/0331390 A1 | 12/2010 | Crooke et al. | |
| 2011/0003713 A1 | 1/2011 | Khvorova et al. | |
| 2011/0189300 A1 | 8/2011 | MacLachlan et al. | |
| 2012/0053128 A1 | 3/2012 | Bhattacharjee et al. | |

FOREIGN PATENT DOCUMENTS

| | | |
|---|---|---|
| WO | WO 9813385 A2 * | 4/1998 |
| WO | WO 2011/029016 | 3/2011 |
| WO | WO 2013/076730 | 5/2013 |

OTHER PUBLICATIONS

Avraham-Davidi et al (Jun. 2012. Nature Medicine. 18(6): 967-973 plus two pages of "Online Methods").*
Phillips, 2001. J Pharm Pharmacology 53: 1169-1174.*
Brandwijk et al. 2006. Trends in Mol Med. 13(5): 200-209.*
Song et al, 2007. International Journal of Nanomedicine. 2(4): 767-774.*
Wells (1990) Biochemistry 29(37): 8509-8517.*
Ngo et al (1994) "The Protein Folding Problem and Tertiary Structure Prediction, Chapter 14: Structure Prediction, and the Levinthal Paradox" pp. 433-440 and 492-495 only. Computational Complexity Protein.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Sullivan, 2015. Low-Denisty Lipoprotein, available on-line at http://www.chemistryexplained.com/Kr-Ma/Low-Density-Lipoprotein-LDL.html; 4 pages as printed.*
International Preliminary Report on Patentability Dated Jun. 5, 2014 From the International Bureau of WIPO Re. Application No. PCT/IL2012/050480.
International Search Report and the Written Opinion Dated Mar. 13, 2013 From the International Searching Authority Re. Application No. PCT/IL2012/050480.
Avraham-Davidi et al. "ApoB-Containing Lipoproteins Regulate Angiogenesis by Modulating Expression of VEGF Receptor 1", Nature Medicine, XP002692898, 18(6): 967-973, Jan. 1, 2012. Supplemental information.
Avraham-Davidi et al. "ApoB-Containing Lipoproteins Regulate Angiogenesis by Modulating Expression of VEGF Receptor 1", Nature Medicine, XP055054549, 18(6): 967-973, Jan. 1, 2012.
Ramunddal et al. "Overexpression of Apolipoprotein-B Improves Cardiac Function and Increases Survival in Mice With Myocardial Infarction", Biochemical and Biophysical Research Communications, XP026281587, 385(3): 336-340, Jul. 31, 2009.

(Continued)

*Primary Examiner* — Zachary Howard

(57) ABSTRACT

A method of treating an angiogenesis related disease or disorder in a subject in need thereof is disclosed. The method comprises administering to the subject a therapeutically effective amount of an agent which regulates an amount of apolipoprotein B (ApoB), and/or an ability of ApoB to transcriptionally control vascular endothelial growth factor receptor 1 (VEGFR1).

3 Claims, 24 Drawing Sheets

(56) References Cited

OTHER PUBLICATIONS

Salomonsson et al. "Oxidised LDL Decreases VEGFR-1 Expression in Human Monocyte Derived Macrophages", Atherosclerosis, 169(2): 259-267, Aug. 2003. Abstract.

Süle et al. Capillary Injury in the Ischemic Brain of Hyperlipidemic, Apolipoprotein B-100 Transgenic Mice, Life Sciences, XP026172303, 84(25-26): 935-939, Jun. 19, 2009.

Cross et al. "Gene Therapy for Cancer Treatment: Past, Present and Future", Clinical Medicine & Research, 4(3): 218-227, Sep. 2006.

Gupta et al. "Human Studies of Angiogenic Gene Therapy", Circulation Research, Journal of the American Heart Association, (105): 724-736, 2009.

* cited by examiner

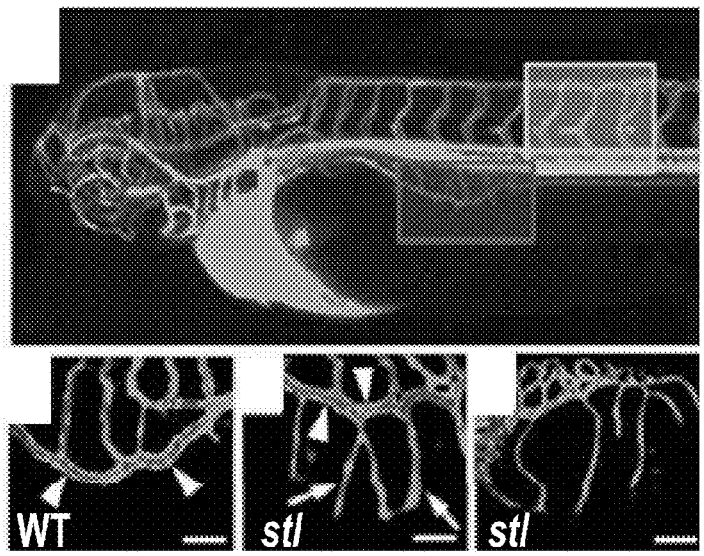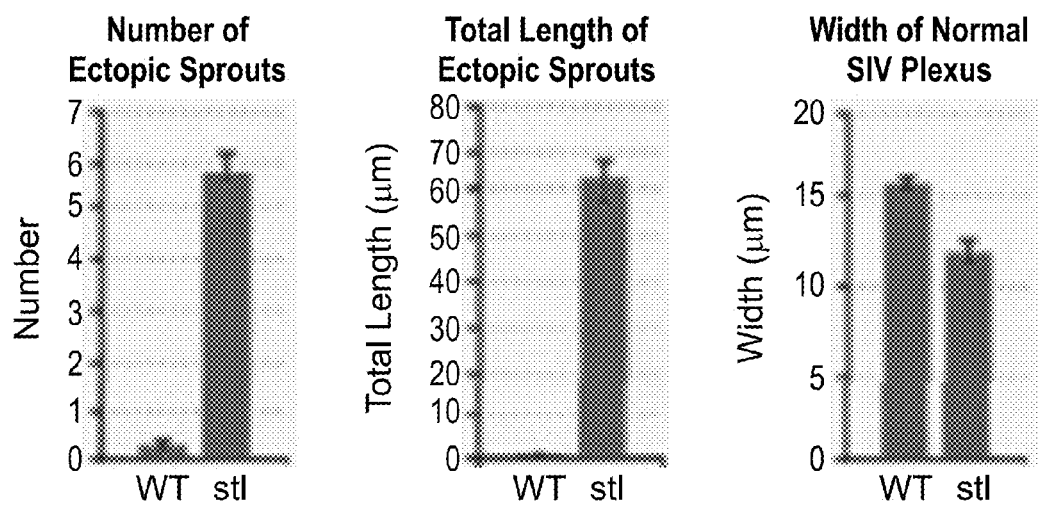

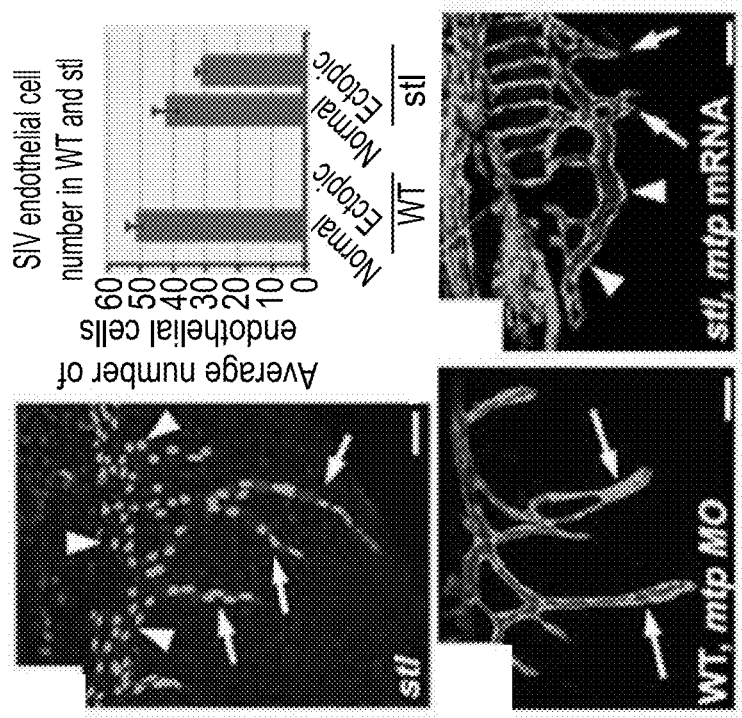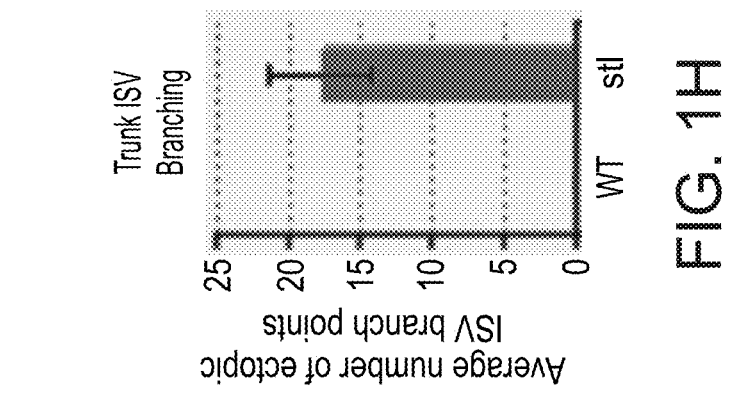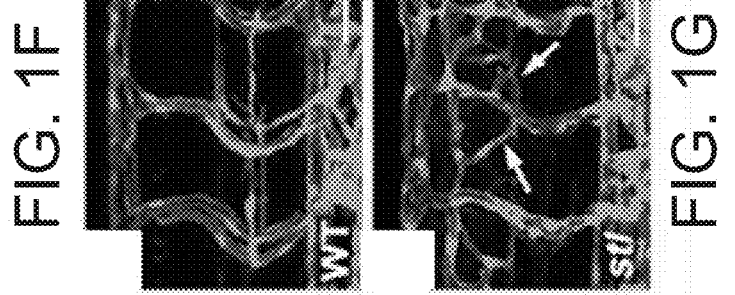

FIG. 1O
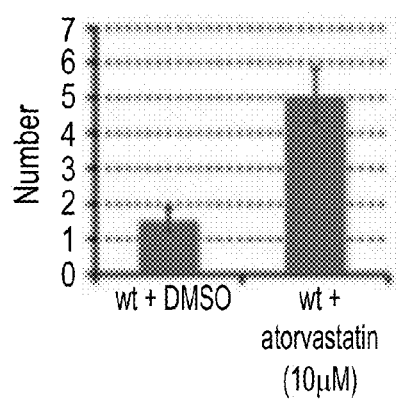
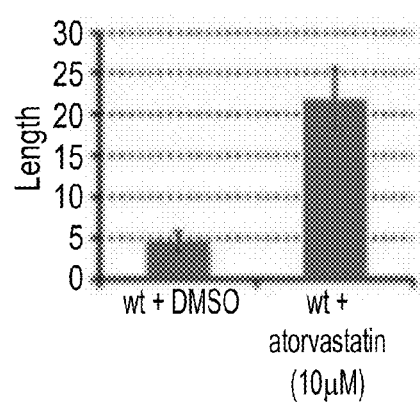

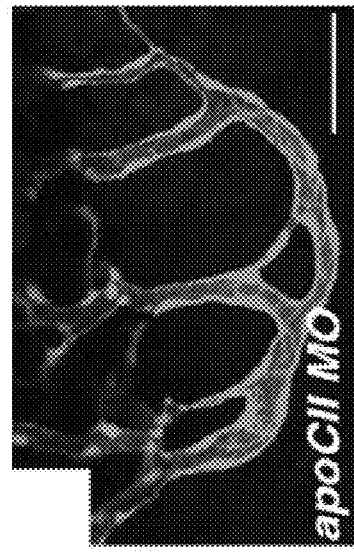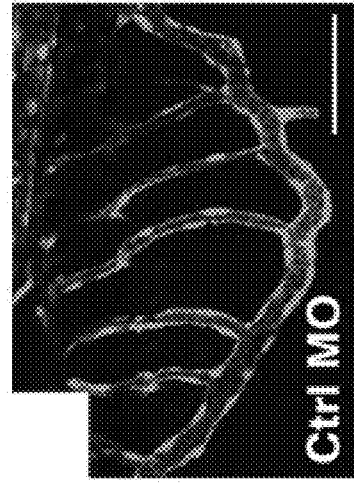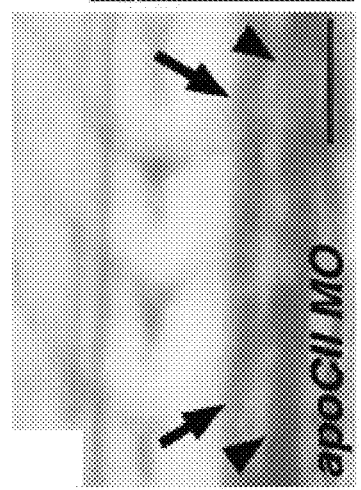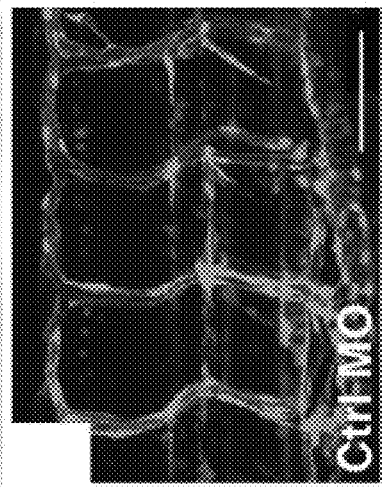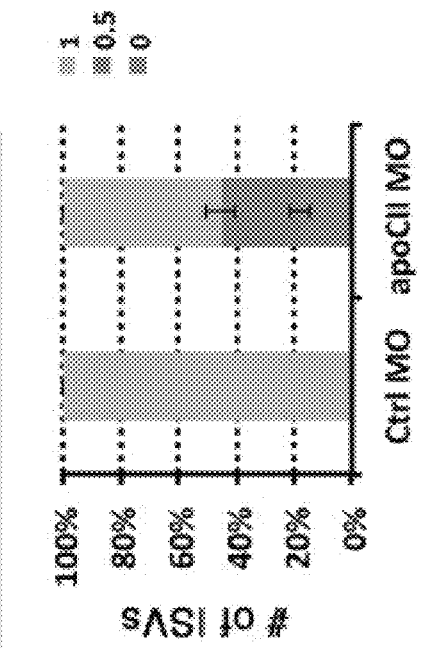
FIG. 2A  FIG. 2B  FIG. 2C  FIG. 2D  FIG. 2E  FIG. 2F

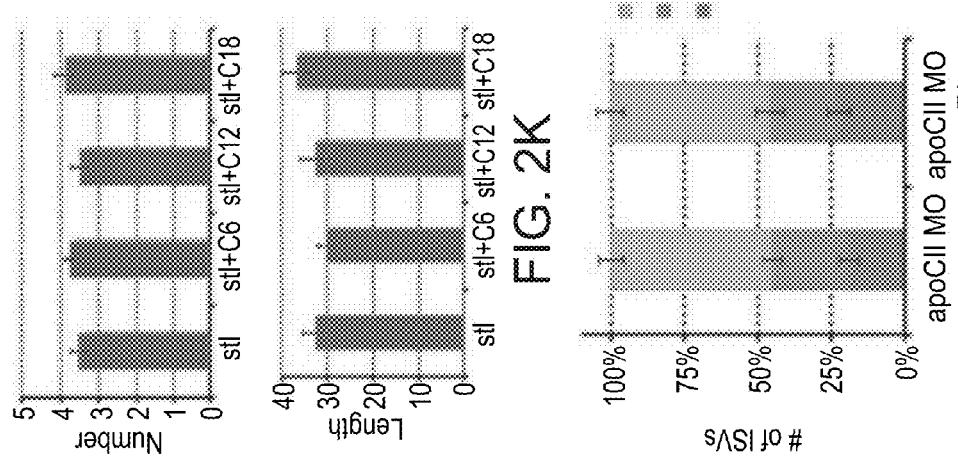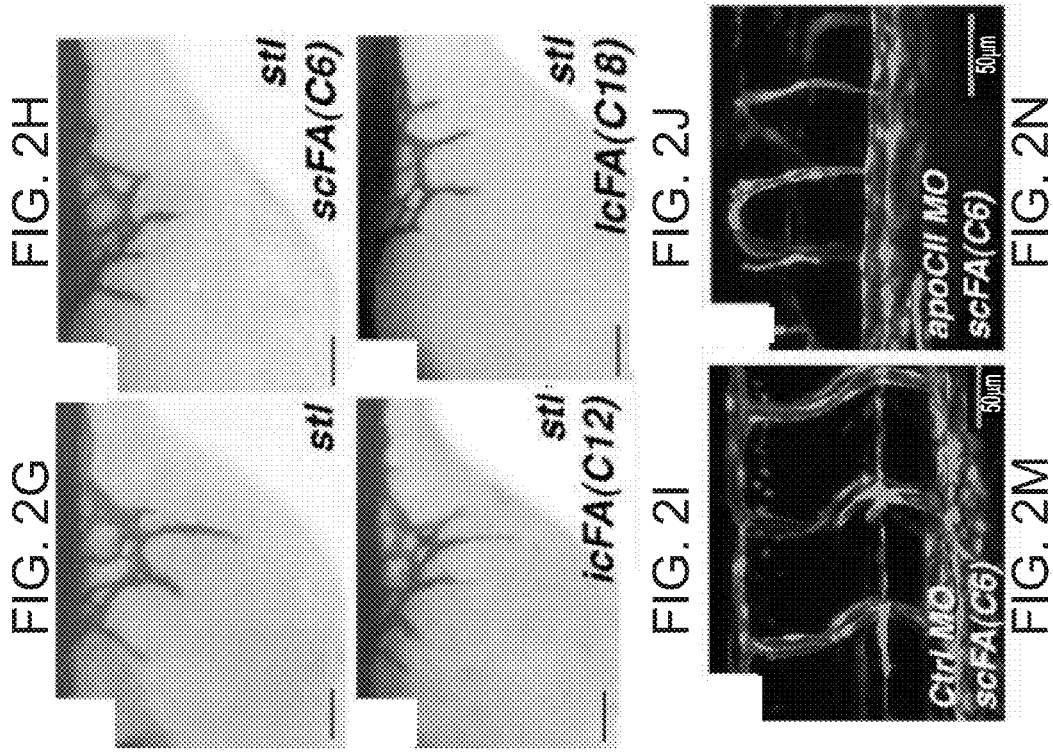

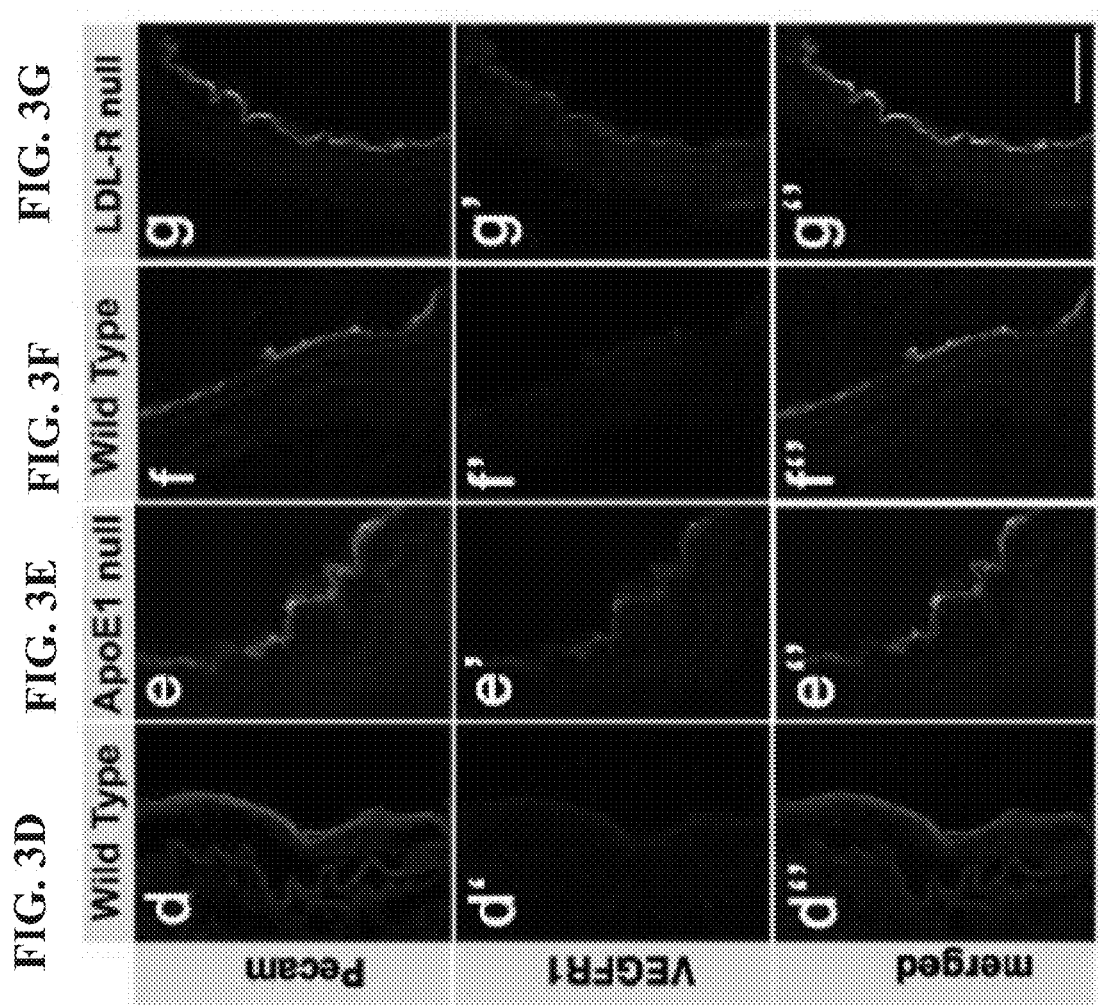

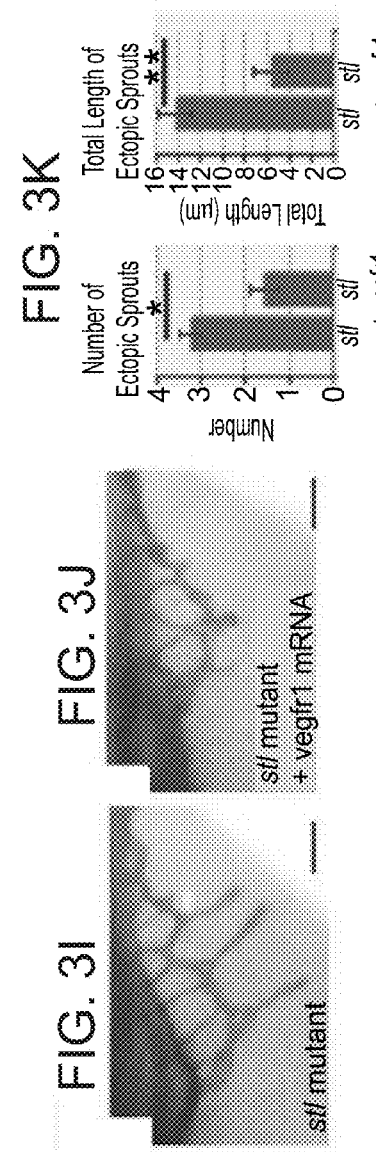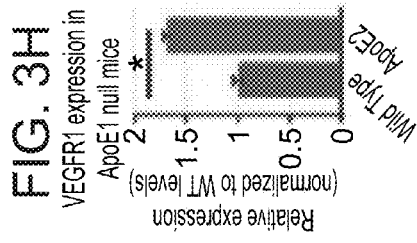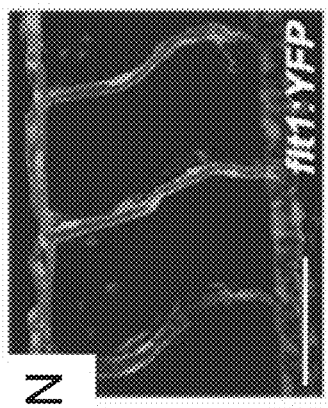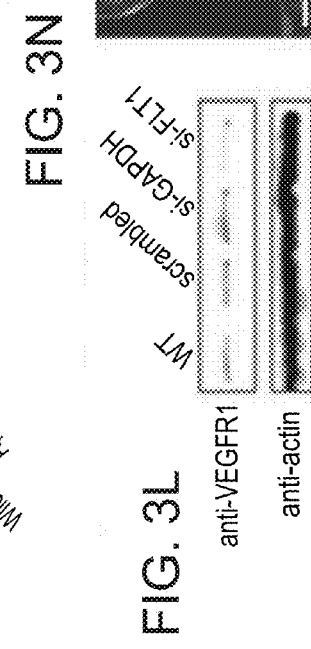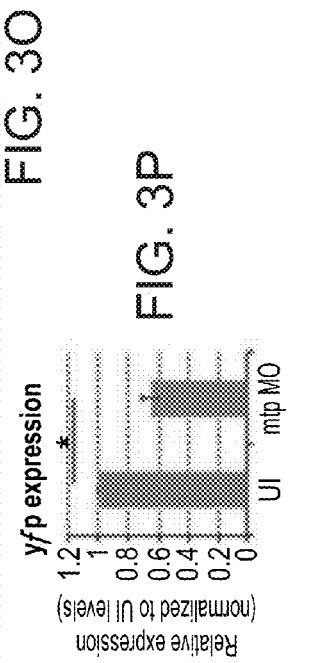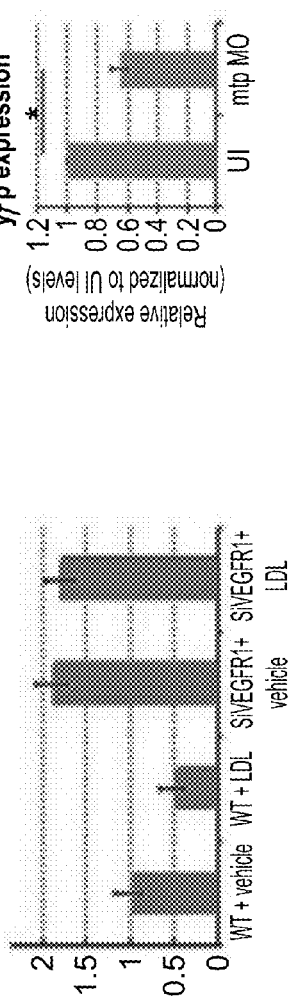

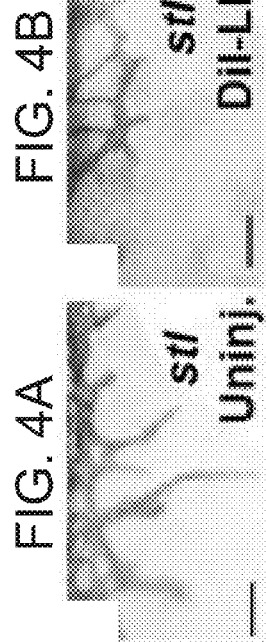
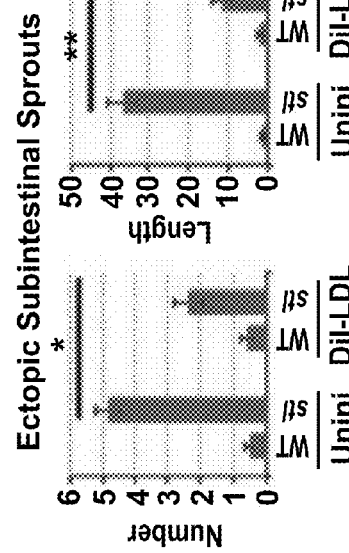
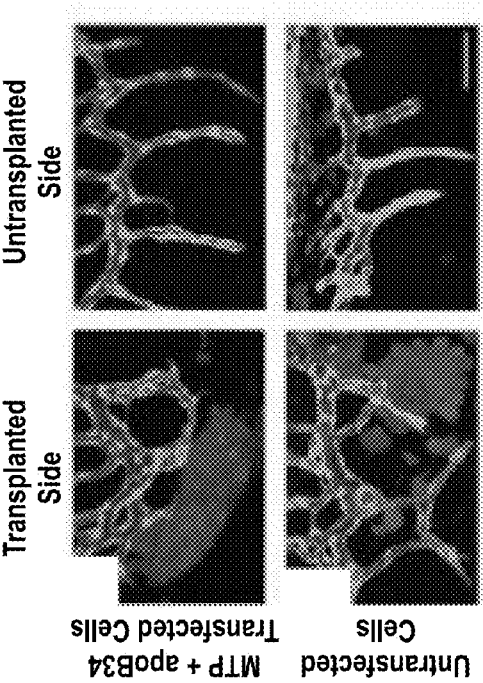
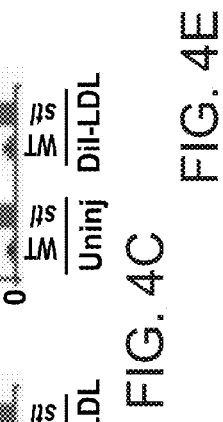
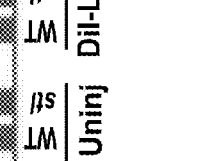
FIG. 4A  FIG. 4B  FIG. 4C  FIG. 4D  FIG. 4E  FIG. 4F

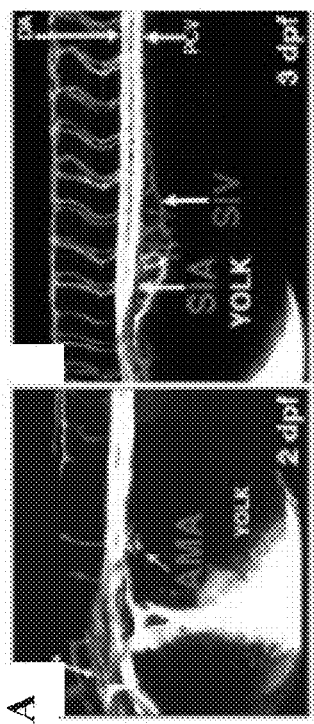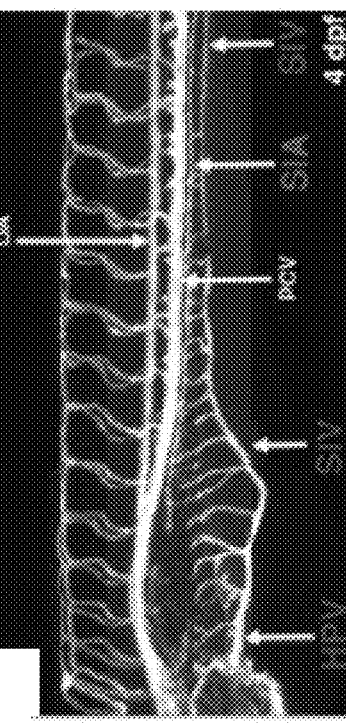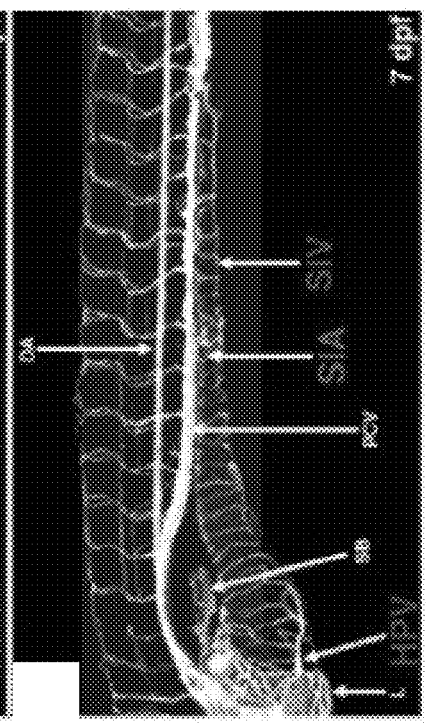
FIG. 5A  FIG. 5B  FIG. 5C  FIG. 5D

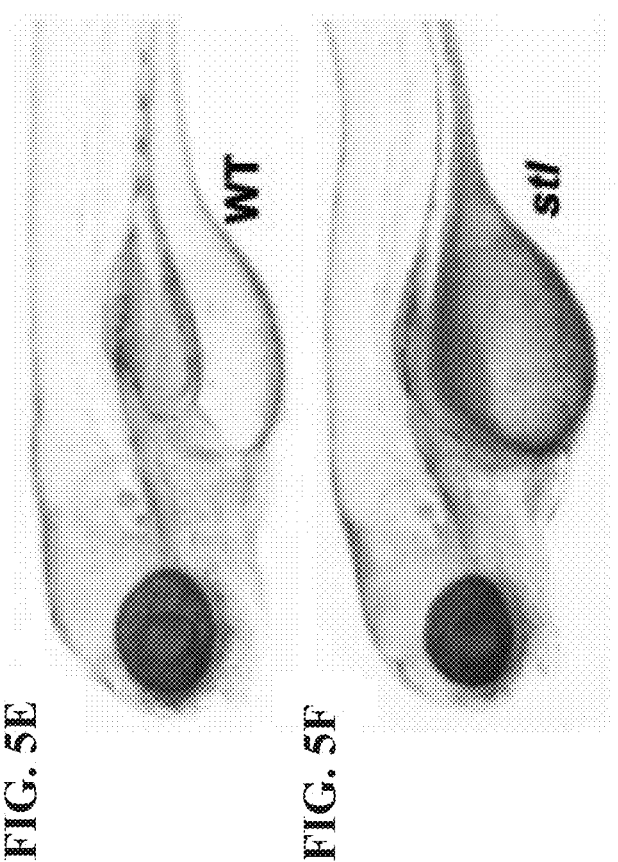

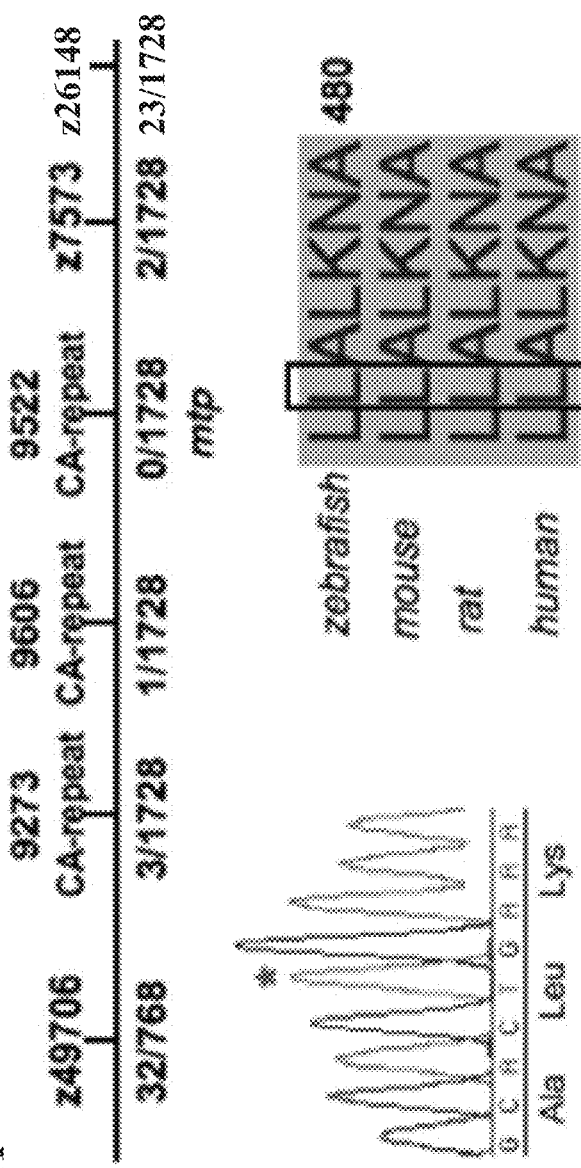
FIG. 7A
FIG. 7B
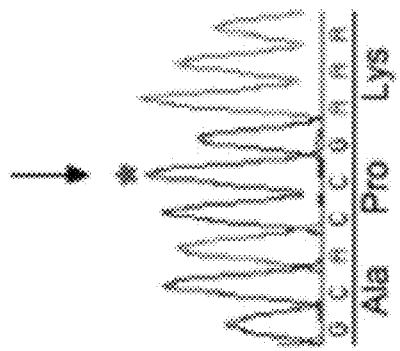
FIG. 7C

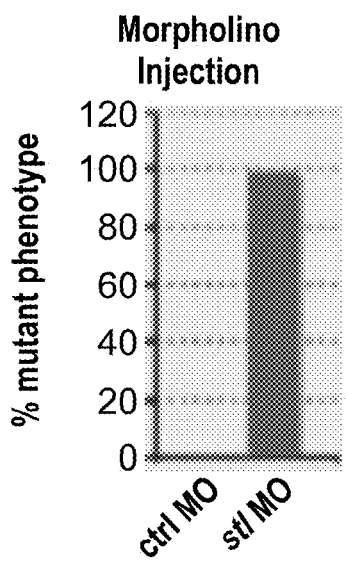
FIG. 8A
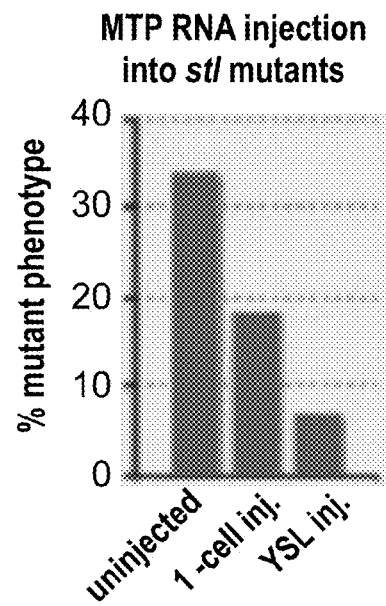
FIG. 8B
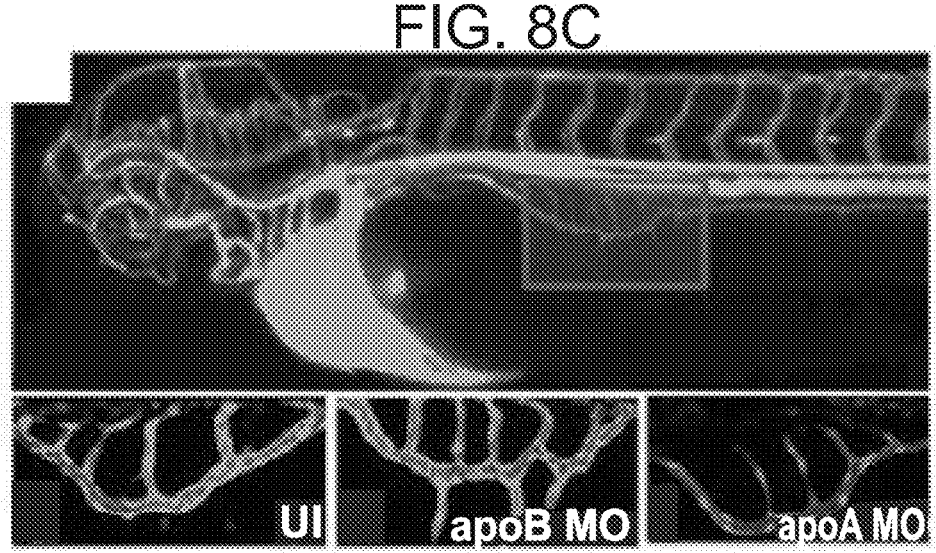
FIG. 8C
FIG. 8D  FIG. 8E  FIG. 8F
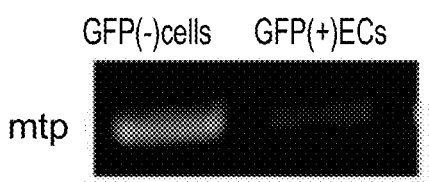
FIG. 8G

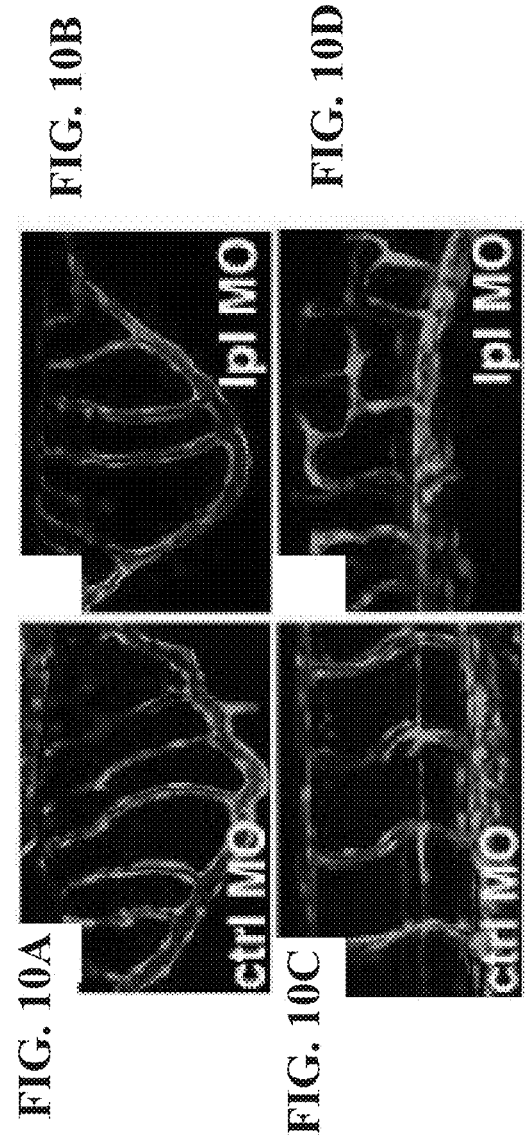

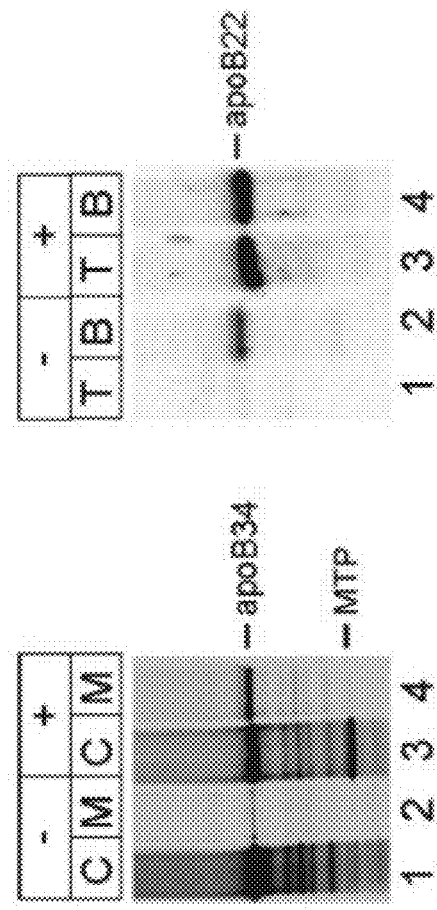

METHODS OF REGULATING ANGIOGENESIS BY ADMINISTERING AGENTS WHICH INCREASE APOB-100 POLYPEPTIDE

RELATED APPLICATIONS

This application is a National Phase of PCT Patent Application No. PCT/IL2012/050480 having International filing date of Nov. 27, 2012, which claims the benefit of priority under 35 USC §119(e) of U.S. Provisional Patent Application Nos. 61/643,429 filed on May 7, 2012 and 61/563,783 filed on Nov. 27, 2011. The contents of the above applications are all incorporated by reference as if fully set forth herein in their entirety.

SEQUENCE LISTING STATEMENT

The ASCII file, entitled 59359SequenceListing.txt, created on May 27, 2014 comprising 47,565 bytes, submitted concurrently with the filing of this application is incorporated herein by reference.

FIELD AND BACKGROUND OF THE INVENTION

The present invention, in some embodiments thereof, relates to methods of regulating angiogenesis by up or down regulation of Apolipoprotein B (apoB).

Angiogenesis is the formation of new blood vessels from pre-existing vasculature. Angiogenesis is relevant not only to cancer but also to non-neoplastic diseases such as: macular degeneration, psoriasis, endometriosis, arthritis and cardiovascular disease. The growth and metastasis of tumors are dependent upon angiogenesis. Therefore, inhibiting angiogenesis can be used as a method of retarding tumor progression.

Endothelial cells are the building blocks of blood and lymphatic vessels. The interaction between vascular endothelial growth factor (VEGF), which is secreted by tumor cells, and their receptors initiates signaling pathways leading to angiogenesis, including tumor-related angiogenesis. VEGF promotes endothelial cell survival, proliferation, and migration, mainly through the activation of the Flk-1 receptor.

Previous studies have shown that vascular endothelial growth factor receptor 1 (VEGFR1) plays an inhibitory role in angiogenesis, acting as a "sink" for the VEGF ligand [Hiratsuka, S., et al., Proceedings of the National Academy of Sciences of the United States of America 95, 9349-9354 (1998); Kearney, J. B., et al. Blood 99, 2397-2407 (2002); Chappell, J. C., et al., Developmental cell 17, 377-386 (2009)].

Apolipoprotein B (apoB) is a non-exchangeable apolipoprotein found associated exclusively with plasma lipoproteins. In the human genome there is one apob gene of less than 45 kb. In the liver, it is transcribed into a single mRNA of 15 kb and is translated into a single polypeptide of 4536 amino acids called apoB-100. In the intestine, the apoB mRNA is post-transcriptionally edited, resulting in the conversion of a glutamine codon into a stop codon. The edited mRNA is translated into a single polypeptide of 2,152 amino acids called apoB48.

Microsomal triglyceride transfer protein (MTP), an intraluminal protein found within the endoplasmic reticulum of liver and intestine, is required for assembly and secretion of proatherogenic-, apoB-containing lipoproteins such as chylomicrons, very low-density lipoproteins (VLDLs), and low-density lipoproteins (LDLs). Following their assembly as mature particles, apoB-lipoproteins are secreted to the blood and lymph stream by MTP.

U.S. patent applications Ser. No. 20110189300 and 20110003713 teach siRNA molecules that silence ApoB expression and methods of using such siRNAs for the treatment of atherosclerosis, angina pectoris, high blood pressure, diabetes, and hypothyroidism.

U.S. patent application Ser. No. 20050222029 teaches a method of treating cancer by preventing the interaction of ApoB with APOA1.

U.S. patent application Ser. No. 20120053128 teaches a method of inhibiting angiogenesis in mammals using a dimer peptide of apolipoprotein E.

Additional background art includes Salomonsson L. et al., Atherosclerosis. 2003 August; 169(2):259-67.

SUMMARY OF THE INVENTION

According to an aspect of some embodiments of the present invention there is provided a method of treating an angiogenesis related disease or disorder in a subject in need thereof, the method comprising administering to the subject a therapeutically effective amount of an agent which regulates an amount of apolipoprotein B (ApoB), and/or an ability of ApoB to transcriptionally control vascular endothelial growth factor receptor 1 (VEGFR1), thereby treating the angiogenesis related disease.

According to an aspect of some embodiments of the present invention there is provided a method of identifying a metastasized cancer in a subject in need thereof, comprising determining the level of ApoB in a fluid sample of the subject, wherein an up-regulation of the level of the ApoB compared to the level of ApoB in the fluid sample of a healthy subject, is indicative of a metastasized cancer.

According to an aspect of some embodiments of the present invention there is provided a method of identifying an agent which regulates angiogenesis comprising:

(a) introducing the agent into a cell;
(b) analyzing VEGFR1 transcription in the cell; and
(c) identifying the agent capable of regulating ApoB-dependent VEGFR1 transcription in the cell, thereby selecting the agent which regulates angiogenesis.

According to an aspect of some embodiments of the present invention there is provided a method of identifying an agent which regulates angiogenesis comprising contacting the agent with a polynucleotide which encodes the 3' untranslated region (UTR) of the ApoB in a cell, wherein the UTR is operatively attached to a reporter molecule, wherein a change in the amount of the reporter molecule is indicative of the agent which regulates angiogenesis.

According to an aspect of some embodiments of the present invention there is provided a method of regulating angiogenesis, the method comprising contacting cells with an agent selected according to the method of the present invention, thereby regulating angiogenesis.

According to some embodiments of the invention, when the regulates is up-regulates, the agent comprises an ApoB polypeptide agent.

According to some embodiments of the invention, when the regulates is up-regulates, the angiogenesis related disease is selected from the group consisting of cancer, arthritis, rheumatoid arthritis, atherosclerotic plaques, corneal graft neovascularization, hypertrophic or keloid scars, proliferative retinopathy, diabetic retinopathy, macular degeneration, granulation, neovascular glaucoma and uveitis.

According to some embodiments of the invention, when the regulates is up-regulates, the angiogenesis related disease is cancer or metastatic cancer.

According to some embodiments of the invention, when the regulates is down-regulates, the agent comprises an antibody directed against the ApoB.

According to some embodiments of the invention, when the regulates is down-regulates, the agent comprises a polynucleotide agent directed against the ApoB.

According to some embodiments of the invention, the polynucleotide agent is selected from the group consisting of an antisense, an siRNA, a DNAzyme and a ribozyme.

According to some embodiments of the invention, when the regulates is down-regulates, the angiogenesis related disease is wound healing, ischemic stroke, ischemic heart disease and gastrointestinal lesions.

According to some embodiments of the invention, the administering is effected in vivo.

According to some embodiments of the invention, the administering is effected ex vivo.

According to some embodiments of the invention, the agent is formulated for ex vivo administration.

According to some embodiments of the invention, the fluid sample is selected from the group consisting of blood, plasma, saliva and urine.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1M:
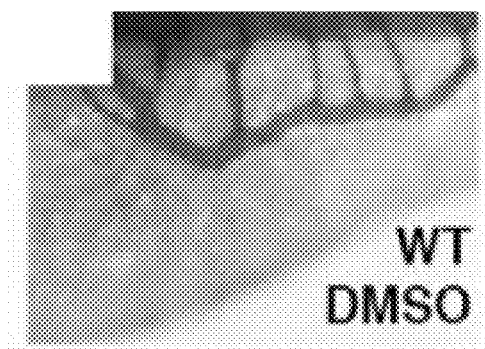
Figure 1N:
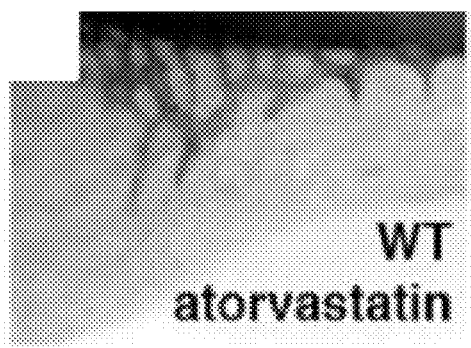
Figure 1P:
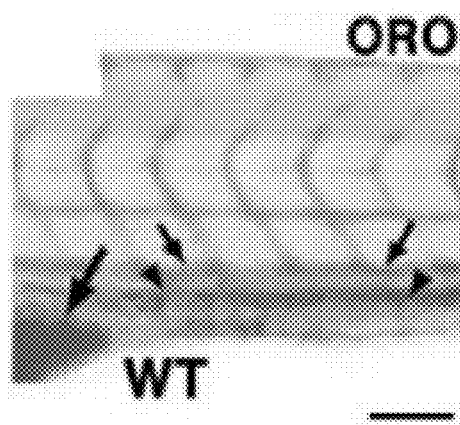
Figure 1Q:
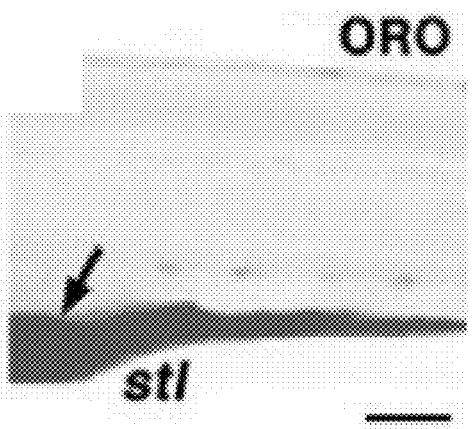

FIGS. 1A-Q illustrate that stl, a zebrafish mutant exhibits excessive angiogenesis. A, Confocal angiography of a 3.5 day post fertilization (dpf) zebrafish, with the subintestinal vessels (SIVs) area shown in (B-D) boxed in red and the intersegmental vessel (ISV) area shown in F,G boxed in yellow. B-D, Confocal images of SIVs in 3.5 dpf (B,C) and 5 dpf (D) wild type (B) and stl mutant embryos (C,D). Note the ectopic angiogenic segments (arrows) that extend ventrally from the normal subintestinal vein (arrowheads). E, Quantitation of the average number (left panel)-, and average total length (middle panel) of ectopic SIV segments, and average width of the normal SIV plexus (right panel) in 3.5 dpf wild type and stl mutant zebrafish. F-G, Confocal images of intersegmental vessels (ISVs) in the mid-trunk of 5 dpf Tg(fli-EGFP)$^{y1}$ wild type (F) and stl mutant (G) embryos, showing ectopic branching in stl mutants (arrows). H, Quantitation of the average number of ectopic ISV branch points in 5 dpf wild type and stl mutant zebrafish. I, Confocal image of SIVs of a 3.5 dpf stl; Tg(fli-nEGFP)$^{y7}$ zebrafish, with individual endothelial cell nuclei clearly visible in both the normal plexus (arrowheads) and ectopic sprouts (arrows). J, Quantitation of the average number of endothelial cell nuclei present in either the normal SW plexus or ectopic SIV sprouts of 3.5 dpf Tg(fli-nEGFP)$^{y7}$ wild type (n=6) or stl mutant larvae (n=7). P=7.3 e$^{-6}$ (t test) K, Confocal image of SIVs in a 3.5 dpf wild type Tg(fli-EGFP)$^{y1}$ zebrafish injected with 4 ng of mtp MO, showing formation of ectopic SW sprouts (arrows) similar to those observed in stl mutants. L, Confocal image of SIVs in a 3.5 dpf stl; Tg(fli-EGFP)$^{y1}$ embryo with 232 pg of mtp mRNA injected into the yolk syncytial layer at dome (approx. 2000-cell) stage, showing reduction in both number and length of ectopic SIV sprouts (arrows) projecting ventrally from the subintestinal vein (arrowheads). M,N, Alkaline phosphatase (AP) staining of SIVs of 3.5 dpf wild type larva that were either treated with DMSO (M) or with DMSO+10 μM atorvastatin (N) at 2.5 dpf. Atorvastatin treatment results in ectopic SW branching. O, Quantitation of the average number (left panel) ($n_{WT+DMSO}$=41, $n_{WT+Atorvastatin}$=38) and average total length (right) ($n_{WT+DMSO}$=39, $n_{WT+Atorvastatin}$=35), of ectopic SIV segments in DMSO or 10 μM atorvastatin treated larvae *p=1.4 e$^{-4}$, ** p=7.7 e$^{-5}$ t-test. P-Q, transmitted light images of 5 dpf Oil Red O (ORO)-stained wild type (P) and stl mutant (Q) larvae, showing strongly decreased lipoprotein levels in the vasculature (arrowheads) of stl mutants. Note normal accumulation of lipids in the yolk of both WT and mutant embryos (arrows). Scale bar in B, C, D, I, K, L 30 μm; in F, G, P, Q 60 μm. All values are mean; error bars show standard deviation of the mean (sdm).

FIGS. 2A-N illustrate that the excess angiogenesis phenotype is not caused by global lipid starvation. A, Transmitted light images of 4 dpf Oil Red O (ORO)-stained apoCII MO-injected larvae, showing increased circulating lipoprotein levels in the dorsal aorta (arrows) and cardinal vein (arrowheads). B-F apoCII morphants show impaired angiogenesis with no ectopic sprouts in the SIVs. B-C, Confocal imaging of SIV in 3.5 dpf Tg(fli-EGFP)y control (B), apoCII (C) MO-injected animals present no ectopic SIV sprouts. D-E, Confocal images of 3.5 dpf control (D) or apoCII MO-injected (E) Tg(fli-EGFP)y zebrafish, showing abnormal trunk ISVs in apoCII morphants. F, Quantitation of trunk ISV's phenotype in control (n=17) and apoCII MO-injected embryos (n=15). Trunk ISV's were classified as 0=no ISV sprouts, 0.5=ISVs up to myoseptum and 1=ISVs up to the Dorsal Longitudinal Anastomotic Vessel (DLAV)). G-K, Free fatty acid supply does not inhibit stl's ectopic sprouts. Alkaline phosphatase (AP) staining of SIVs of 3.5 dpf st/ mutants that were either not treated (G) or treated with 6μg/ml short chain fatty acids (scFA) (C6) (H) intermediate chain fatty acid (icFA) (C12) (I) or long chain fatty acid (lcFA) (J). Treatment with free fatty acids did not inhibit the ectopic vessels phenotype observed in stl mutants. K, Quantitation of the average number (upper panel) and average total length (lower panel) of ectopic SIV segments in 3.5 dpf st/ mutants that were either not treated (n=27) or treated with 6 μg/ml short chain fatty acid (scFA) (C6) (n=29), intermediate chain fatty acid (icFA) (C12) (n=21) or long chain fatty acid (lcFA) (C18) (n=17). (*p =0.517, p=0.5058, *p =0.1479) (ANOVA). 1-n, Free fatty acid supply does not rescue the abnormal ISVs phenotype of apoCII morphants. L, Quantitation of trunk ISV's phenotype in apoCII MO-injected embryos that were soaked either in normal medium (n=15) or in medium supplemented with 6 µg/ml short chain fatty acid (scFA) (C6) (n=17). Trunk ISV's were classified as 0=no ISV sprouts, 0.5=ISVs up to myoseptum and 1=ISVs up to DLAV) M, N, Confocal images of trunk ISV's of 3.5 dpf control (M) or apoCII MO -injected (N) embryos treated with 6µg/ml (C6). No phenotypic changes were detected upon scFA treatment (compare e,m). p=0.839 $x^2$ test. Scale bar in A, B, C, G, H, I, J 30 µm; in D, E 60 µm. All values are mean; error bars show standard deviation of the mean (sdm).

Figure 3A:
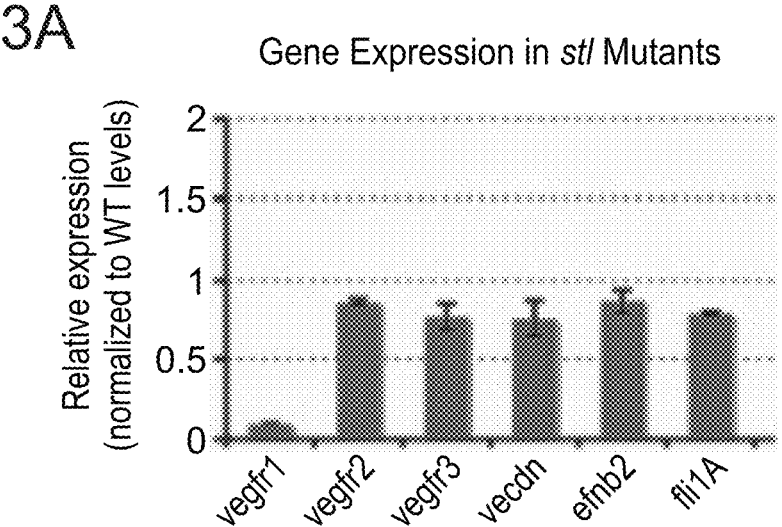

FIGS. 3A-P illustrate that lipoprotein levels regulate VEGFR1 expression. A, qRT-PCR measurement of the expression of selected genes in 24 hpf mtp MO injected vs. uninjected zebrafish embryos. Relative expression levels in MO injected embryos are normalized to wild type expression levels. vegfr1 expression is strongly reduced. B, Vegfr1 and Tubulin (control) protein levels in extracts from 3 dpf zebrafish, measured by probing western blots with anti-zebrafish Vegfr1 and anti-Tubulin antibodies. Levels of Vegfr1 protein are reduced in stl and cloche (clo) mutants (clo mutants lack most endothelium) and increased in apoCII morpholino-injected zebrafish compared to wild type siblings. C, Levels of VEGFR1 and VEGFR2 protein in confluent HUVECs, cultured in LDL-depleted media with or without addition of LDL (5 or 10 µg/ml). Actin protein was probed as a control. Only VEGFR1 expression is upregulated in HUVECs treated with LDL. D-H, Endothelial VEGFR1 expression is upregulated in hyperlipidemic mice. D-G, Confocal images of the aortic root of wild type C57B1/6 sibling (D) or ApoE null (E) mice, and abdominal Aorta of wild type C57B1/6 sibling (F) or LDLR null (G) mice, stained with Pecam (D-G) and anti-VEGFR1 antibody (D'-G'). VEGFR1 is specifically upregulated in endothelial cells of hyperlipidemic mice as denoted by co-localization with Pecam staining (D"-G"). Scale bar presented in G" refers to images D-G, 25 µm. H, Semi-quantitative RT-PCR measurement of vegfr1 expression in aortic arches dissected from wild type sibling (n=4) or apoE null (n=4) mice. $p=4\ e^{-14}$ z test. I-K, vegfr1 inhibits excessive angiogenesis in stl mutants. I, J, Transmitted light images of AP stained SIVs in 3.5 dpf stl mutants (I) or stl mutants injected with vegfr1 mRNA (J), showing that vegfr1 overexpression suppresses ectopic sprouting in stl mutants. K, Quantitation of the average number (left panel)-, and average total length (middle panel) of ectopic SIV segments, and average width of the normal SIV plexus (right panel) in 3.5 dpf stl mutants (n=26) and stl mutants injected with vegfr1 mRNA (n=23). $*p=1.6\ e^{-4}$, $p=2.6\ e^{-4}$, $*p=0.21$ t test. L, M, LDL exposure suppresses VEGFR-mediated endothelial migration. HUVECs exposed to either siRNA control (non-targeting) or siRNA for VEGFR1 were plated to confluency for wound assays. A 200 um wound was inflicted in both groups and each was treated with either LDL or vehicle. Migration of cells was recorded for 24 hrs (note proliferation cycle of these cells ranges from 36 to 48 hrs). Four wells per experimental group were measured. Results were normalized to control and expressed as migration area over control. Bars represent mean (+/− SE). N-P, vegfr1 is transcriptionally regulated. N, O, Confocal images of Tg(flt1:YFP)$^{hu4624}$ wt (N) and mtp MO injected (O) zebrafish. YFP expression is downregulated in mtp morphants. P, qRT-PCR measurements of the relative expression levels of YFP in 48 hpf wt and mtp MO injected Tg(flt1:YFP)$^{hu4624/+}$ zebrafish. The levels of yfp mRNA are strongly reduced in mtp morphants. p=0.0248 t test. Scale bar in I, J, 30 µm, in N, O, 60 µm.

FIGS. 4A-L illustrate that apoB particles regulate angiogenesis by directly acting on endothelial cells. A, B, DiI-LDL inhibits excessive angiogenesis in stl mutants. Alkaline phosphatase (AP) staining of SIVs of 3.5 dpf stl mutants that were either not injected (n=27) (A) or injected intravascularly with DiI-LDL (n=35) (B) at 2.5 dpf. Note the lack of ectopic sprouts observed in treated embryos. C, Quantitation of the average number (left panel) and average total length (right segment) of ectopic SIV segments in 3.5 dpf stl mutants that were either not injected or injected with DiI-LDL. $*p=0.0001$ $**p=3\ e^{-6}$ t test. D, Diagram illustrating the procedure used for transplanting transfected HEK293 cells into the extracellular space between the yolk cell membrane and the outer periderm of zebrafish larva, in close proximity to the SIVs. E,F, Confocal images of the SIVs (green) of 3.5 dpf Tg(fli EGFP)y$^1$ zebrafish transplanted with either MTP and ApoB34 transfected (E)-, or untransfected control (F)-HEK293 cells (red), on one side of the yolk ball. Both, control-untransplanted (E, F right), and transplanted (E, F left) sides of the animal are shown. Only lipoprotein-secreting cells impeded the migration of endothelial cells and the growth of ectopic sprouts in the area of transplantation (E, left panel). G, Quantitation of the overlapping area between SIV endothelium and HEK293 cells in 3.5 dpf transplanted zebrafish as a function of the total length of the interface between the two cell populations. H-K, apoB but not short chain fatty acid (scFA) inhibits excessive angiogenesis in stl mutants. AP staining of SIVs of 4.5 dpf stl mutants that were either not injected (n=16) (H) or injected intravascularly with 6 µg/ml short chain fatty acid (scFA) (n=10) (I) or a delipidated form of apoB-100 (n=24) (J) at 2.5 dpf. Note the lack of ectopic sprouts observed in apoB-injected embryos. K, Quantitation of the average number (left panel) and average total length (right segment) of ectopic SIV segments in 3.5 dpf stl mutants that were either not injected or injected intravascularly with 6 µg/ml short chain fatty acid or a delipidated form of apoB-100. $*p=0.0411$ $**p=4.6\ e^{-5}$ t test 1, Schematic model illustrating the effects of circulating lipoproteins on angiogenesis. Scale bar in A, B, H, I, J 30 µm. Scale bar presented in F (right panel) refers to images E, F, 60 µm. n.s, not significant.

FIGS. 5A-F illustrate the development of the subintestinal vessels (SIVs) and absorption of yolk. A, B, Zebrafish SIVs begin to form at 2.5 dpf, from vascular sprouts that emerge from the supraintestinal artery (SIA) at the ventral midline of the trunk and then grow bilaterally onto the dorsolateral surface of the large yolk cell of the fish (AMAAnterior Mesenteric Artery, PVC—Posterior Cardinal Vein, DA—Dorsal Aorta). C. At 4 dpf the subintestinal vein (SIV) delimits the ventral edge of this vascular bed. The most rostral unbranched portion of the left SIV will become the hepatic portal vein (HPV). D. The yolk is gradually absorbed to supply the growing larva, and by 7 dpf the SW s surround and perfuse the well-differentiated intestine, liver (L) swim bladder (SB) and pancreatic anlagen. E, F, Yolk is absorbed in wild type animals (E), but remains rounded and unabsorbed in stalactite (stl) mutants (F). Scale bar 60 µm.

Figure 6:
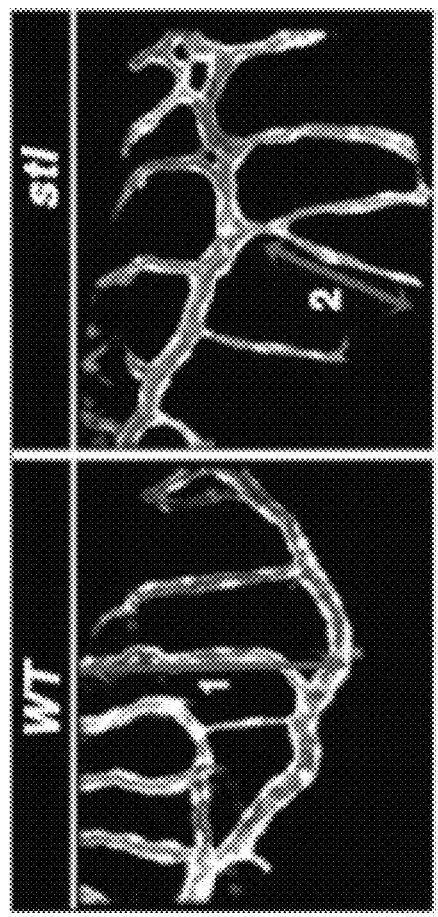

FIG. 6 illustrates quantitation of SW vascular plexus width and ectopic ventral SW sprout number and length. The maximal width of the normal SIV plexus is measured from supraintestinal artery to subintestinal vein (1). The number of ectopic sprouts greater than 1 µm in length projecting ventrally from the subintestinal vein is counted, and the total length of all of these sprouts (2) is measured. Measurements are performed on the SIV vessels of at least 10 animals per treatment, and standard errors of the mean are calculated for these measurements and used in the plots displayed. Scale bar 30 μm.

FIGS. 7A-C illustrates the defect in the microsomal triglyceride transfer protein (mtp) gene, identified by molecular cloning of the stl mutation. A. Interval in linkage group 1 containing the mtp gene. Polymorphic markers used in this study are shown above the map, whereas numbers below the map indicate number of recombinants over the number of informative meioses. B. Sequence analysis of mtp cDNA from stl mutants and wild type siblings reveals a T=>C base change causing a Leu475=>Pro change in the encoded polypeptide. c. Leucine 475 is a highly conserved amino acid residue in the MTP polypeptide.

FIGS. 8A-G illustrates the phenotype of stl mutants. A, Quantitation of the percentage of 3.5 dpf Tg(fli-EGFP)$^y$ uninjected control (n=97) or mtp MO injected (n=98) zebrafish displaying mutant phenotype (ectopic SW sprouts). b, Quantitation of the percentage of larvae from an stl/+ incross (25% of embryos are stl/stl) that display mutant phenotype (ectopic SIV sprouts) with either no mRNA injected (n=104), or 232 pg mtp mRNA injected into the 1-cell stage cytoplasm (n=49) or injected into the dome stage yolk syncytial layer (n=29). C, Confocal angiography of a 3.5 dpf zebrafish, with the subintestinal vessels (SIVs) area shown in (D-F) below boxed in red. (D-F) Confocal images of the SIVs in 3.5 dpf Tg(fli-EGFP)y$^1$ zebrafish un-uninjected (D) or injected with either apoB (E) or apoA1 Morpholinos (F). Ectopic SIV sprouts are observed in apoB MO-injected embryos, reminiscent of those seen in stl mutants. apoA1 morphants, however, do not exhibit any morphological change even when injected with high concentration of morpholino. G, mtp is not expressed by zebrafish EC's. GFP$^+$ ECs and GFP$^-$ cells from 3.5 dpf Tg(fli-EGFP)y$^1$ zebrafish were FACS sorted and their mRNA was used for semi-quantitative RT-PCR. mtp was found to be expressed by GFP$^-$ cells but not by GFP$^+$ ECs. Scale bar in C—60 μm; in D, E, F 30 μm.

Figure 9A:
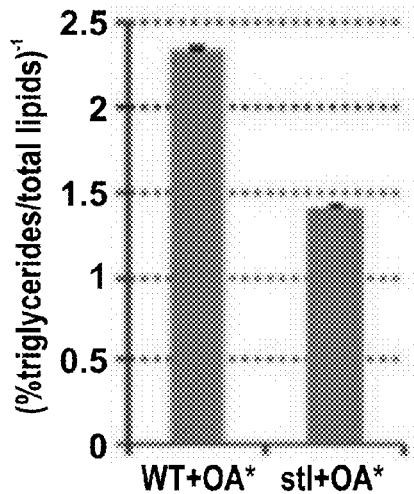
Figure 9C:
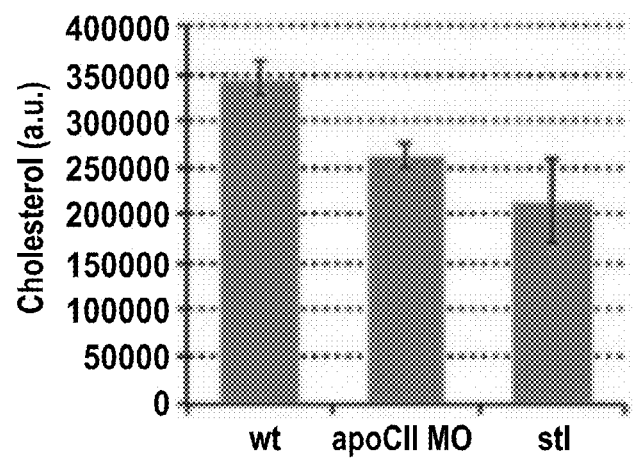
Figure 9B:
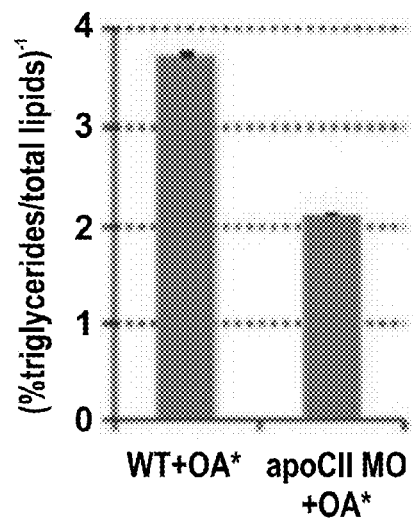

FIGS. 9A-C are graphs illustrating that the cells of stl mutants and apoCII morphants are starving for lipids. (A, B) Dechorionized 24 hpf stl mutants, apoCII MO-injected and WT embryos were soaked in 2 μCi/ml$^3$ Holeic acid for 48 hours. Embryo lipid extracts were developed on silica gel 60 TLC plates and spots corresponding to triglyceride standards were quantified. Exogenously supplied radiolabeled fatty acids were incorporated at higher rates in both stl mutants (n=93) and ApoCII morphants (n=60) as opposed to WT embryos (n=93 in A and n=65 in B), indicating that cells are lipid-starved in both models. $P_a$=2 e$^{-12}$, $P_b$=8 e$^{-17}$; t test. (C) Total cholesterol levels in wild type, apo CII morphants and stl mutants were analyzed using gas chromatography-mass spectrometry (GC-MS). Cholesterol levels are reduced in apoCII morphants and stl mutants when compared to WT siblings.

FIGS. 10A-D are photographs illustrating that downregulation of lpl results in poorly developed vasculature with no ectopic SIV sprouts. A,B, Confocal imaging of SIV in 3.5 dpf Tg(fli-EGFP)y$^1$ control (A) or lpl MO-injected (B) animals present no ectopic SIV sprouts. C, D, Trunk ISVs in 3.5 dpf Tg(fli-EGFP)y control (C) or lpl-MO injected zebrafish larvae. Lpl morphants display short and partially lumenized ISVs.

Figure 11:
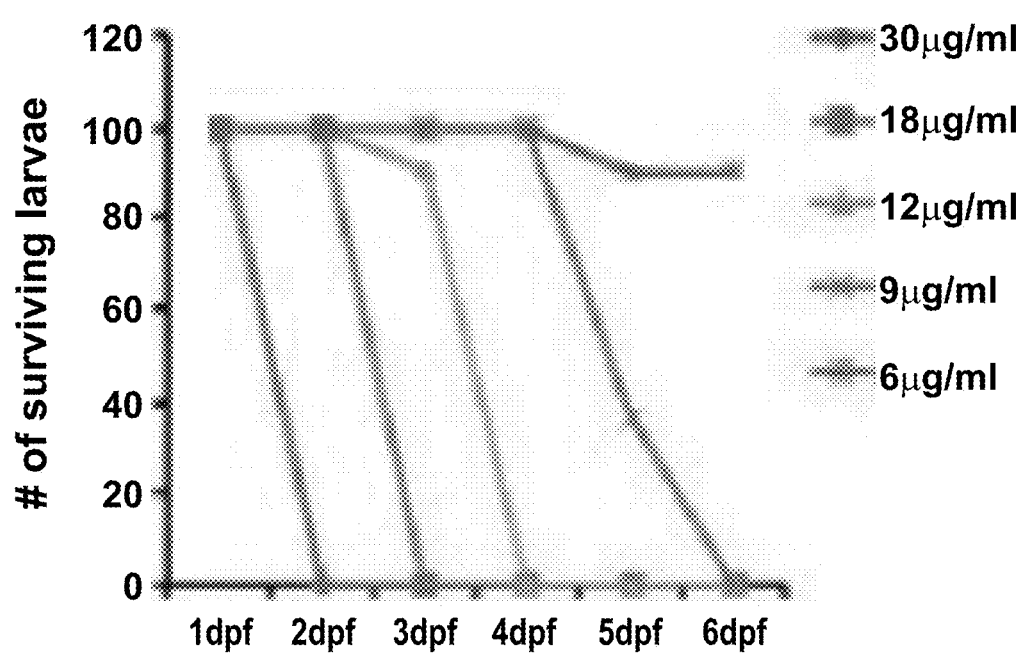

FIG. 11 is a survival curve of WT zebrafish embryos treated with increasing concentrations of oleic acid. Only embryos treated with less than 6 μg/ml oleic acid survived until 6 dpf.

Figure 12:
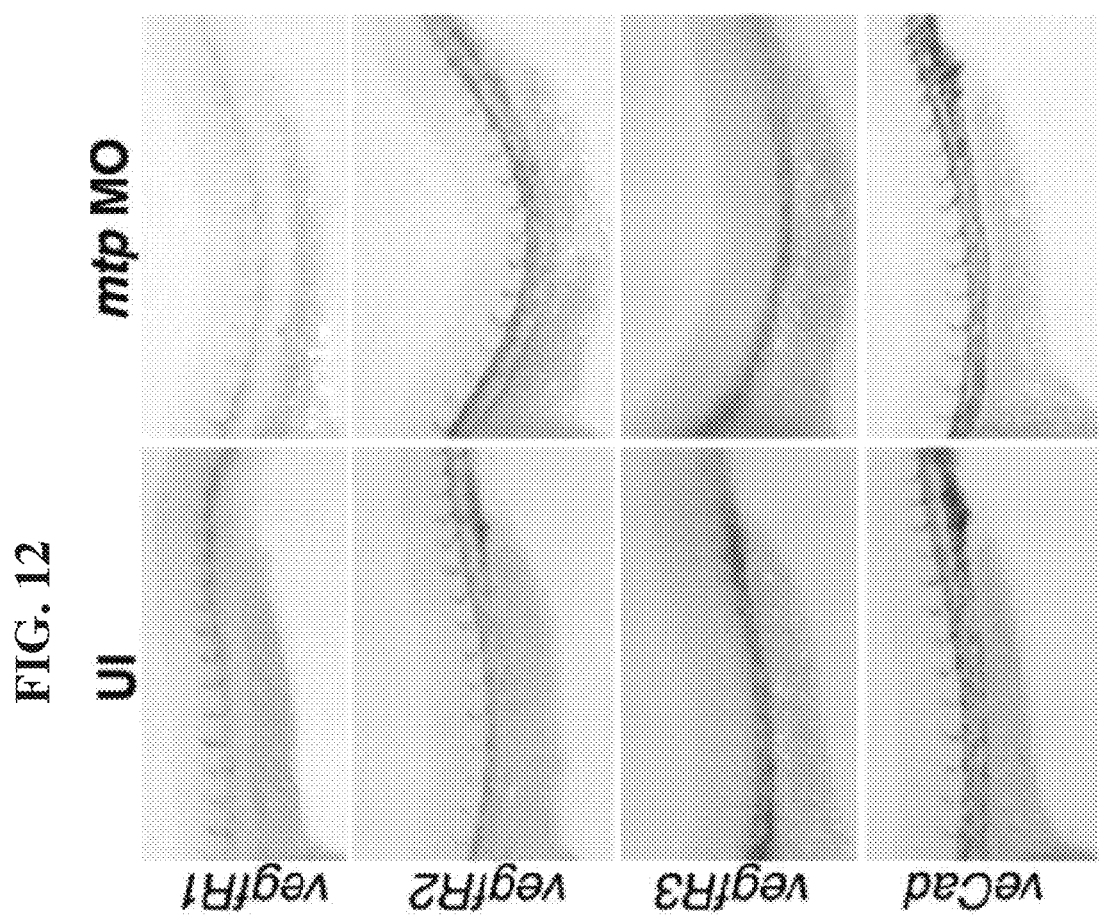
Figure 13A:
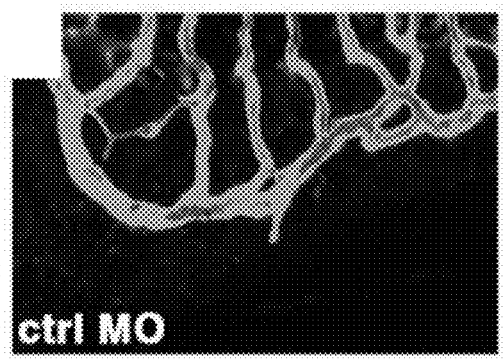
Figure 13B:
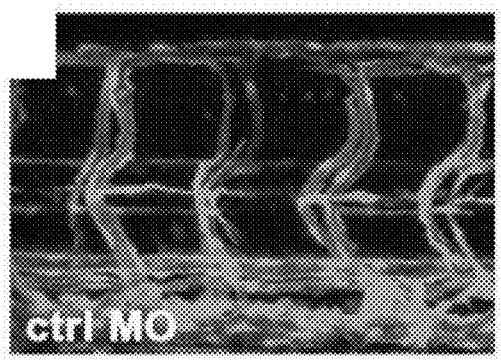
Figure 13C:
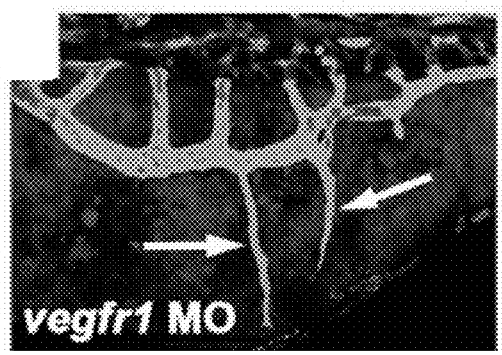
Figure 13D:
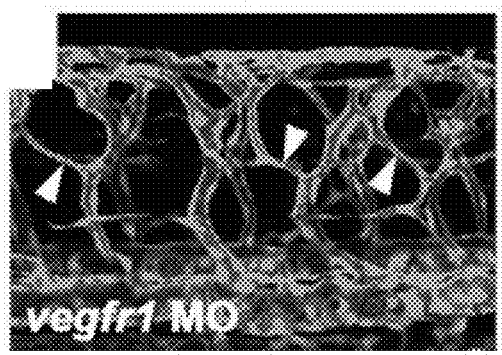
Figure 13E:
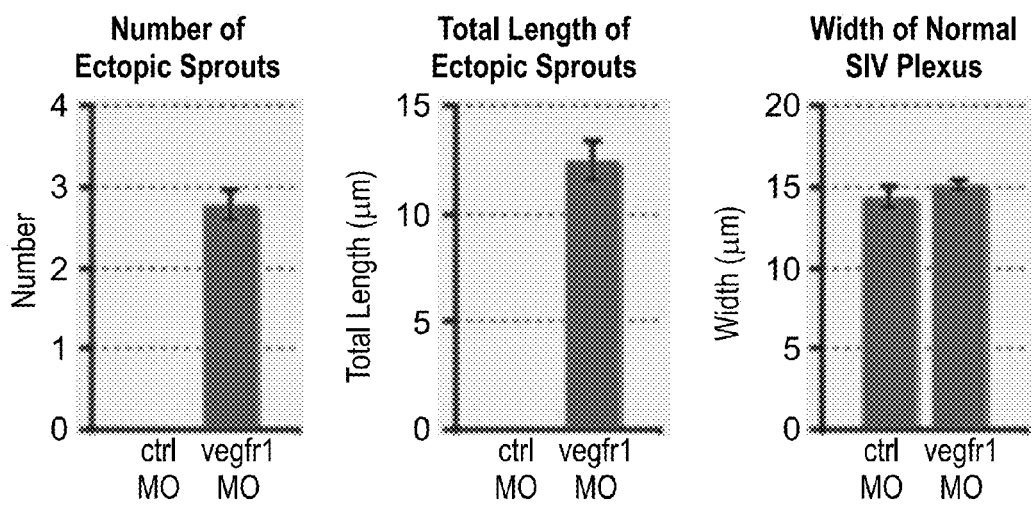

FIG. 12 illustrates vegfr1 expression is specifically reduced in mtp-MO injected zebrafish. In situ hybridization of control un-injected (left panels) or mtp MO-injected (right panels) 24 hpf zebrafish, probed for vegfr1, vegfr2, vegfr3, or veCad showing specific increase in vegfr1 mRNA levels. Scale bar 60 μm.

FIGS. 13A-E illustrate the vessels of control or vegfr1 morpholino-injected animals. A, C, Confocal imaging of SIVs in 3.5 dpf Tg(fli-EGFP)y control (A) or vegfr1 (C) morpholino-injected animals, showing ectopic SIV sprouts in vegfr1 morphants (arrows) similar to these observed in stl mutants. B, D. Confocal images of vessels in the mid-trunk of the same embryos showing ectopic branching and sprouting (arrowheads) in vegfr1 MO-injected embryo. E. Quantitation of the average number (left panel), average total length (middle panel) of ectopic SW segments, and average width of the normal SIV plexus (right panel) in 3.5 dpf control and vegfr1 MO-injected zebrafish larvae. Scale bar in A, C 30 μm; in B, D 60 μm.

FIGS. 14A-B illustrates that Huh7MTP promotes the lipidation and the secretion of apoB34. A, ApoB34 was transfected into HEK293 cells without (−) or with (+) Huh7MTP, as indicated. Twenty-four hours posttransfection cells were radiolabeled with $^{35}$[S]Met and Cys for 3 hours and cell lysate (C) and media (M) samples subjected to immunoprecipitation with anti-apoB antibody, followed by 8% SDS-PAGE and phosphorimager analysis. Cotransfection with Huh7MTP resulted in an ~5-fold increase in apoB34 secretion relative to control cells (compare lanes 2 and 4). Huh7MTP interacted with apoB intracellularly as evidenced by its co-immunoprecipitation with anti-apoB antibody (lane 3). B. Huh7MTP promotes the lipidation of ApoB22. ApoB22 was cotransfected without (−) or with (+) Huh7MTP, as indicated. 24 hours post-transfection, cells were radiolabeled with 35[S]Met and Cys for 3 hours. Media was adjusted to 1.25 g/ml with KBr and subjected to equilibrium density gradient centrifugation. The top (T) buoyant fractions and bottom (B) lipid-poor infranatant fractions were subjected to immunoprecipitation with anti-apoB anybody, fractionation by 12.5% SDS-PAGE and phosphorimager analysis. ApoB22 was found in the top buoyant fraction only upon coexpression with Huh7MTP (compare lanes 1 and 3).

Figure 15:
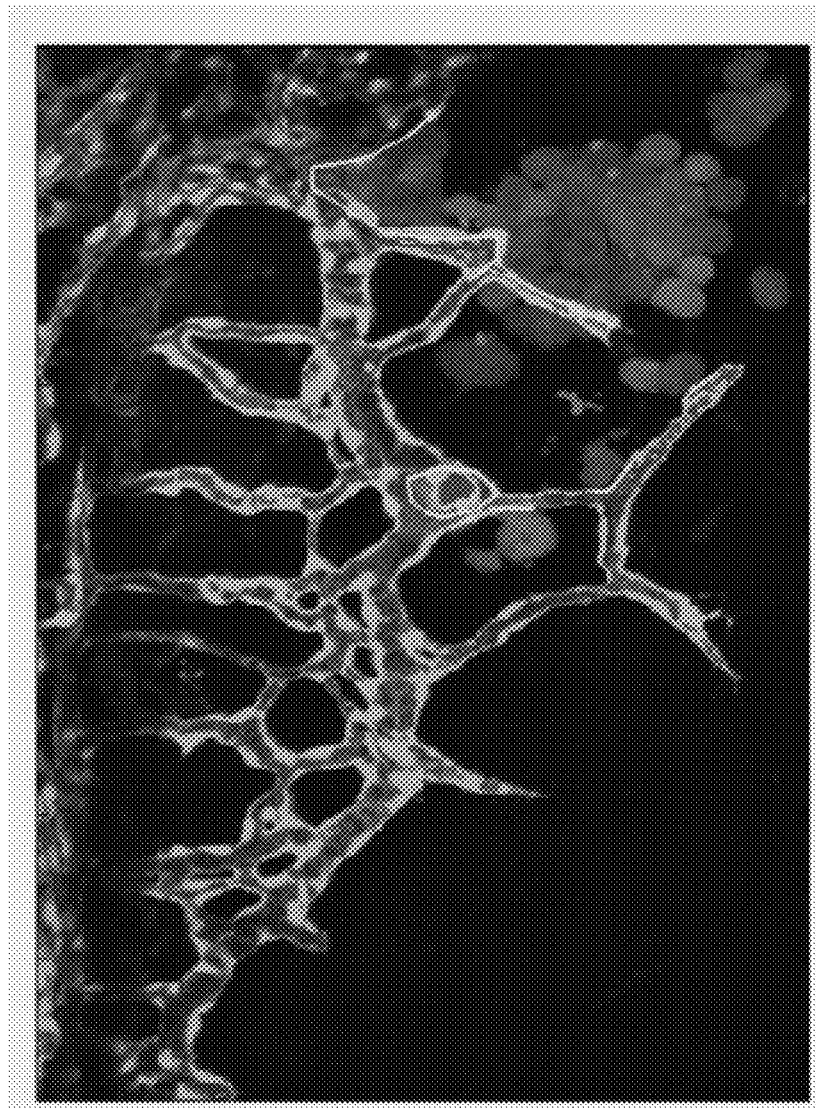

FIG. 15 is a quantitative analysis of HEK293 cell transplants. Screen output illustrating the use of a software tool developed for the purpose of quantifying the effects of exogenous secreted lipoproteins on zebrafish blood vessels. Yolk region of a Tg(fli:EGFP)y$^1$ embryo, showing transplanted HEK293 cells (red) and subintestinal vessels (green). Phenotypic quantitation was performed at 3.5 dpf only in embryos that had been successfully transplanted with fluorescent red cells adjacent to green fluorescent endothelial cells. The total length of the interface between endothelial and transplanted cells (L1, blue), as well as the total length of overlapping between the two cell populations (L2, yellow) were traced and measured. We then used the ratio r=L2/(L1+L2) as a measure of the tendency of endothelial cells to penetrate the ApoB secreting cells area (once in their vicinity). The ratios were computed for three transplanted animals per treatment (transfected and untransfected HEK293 cells), and were compared using t-test.

Figure 16B:
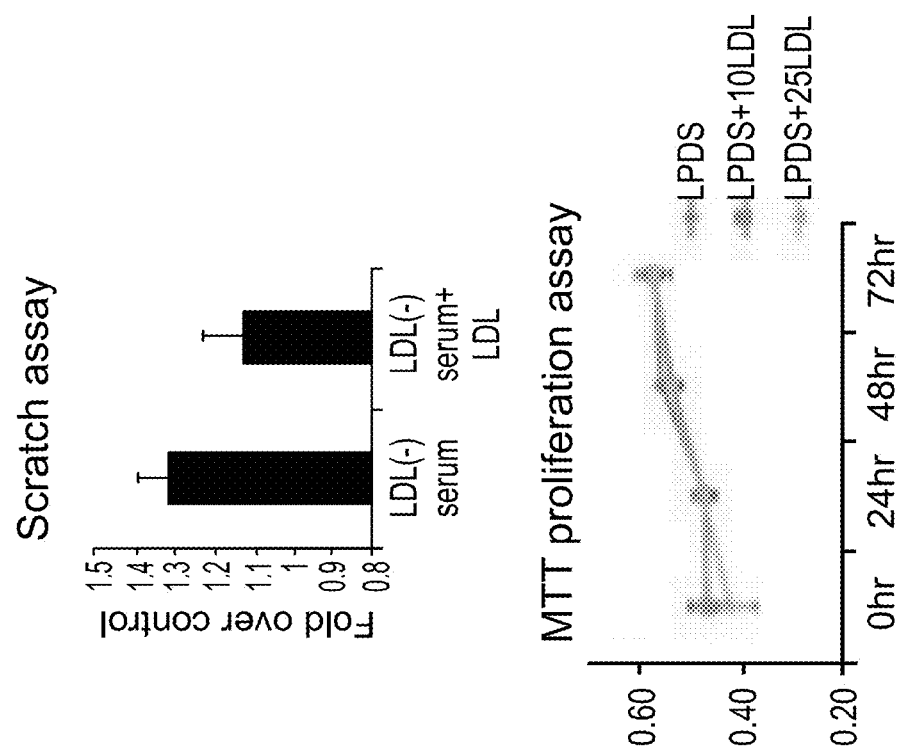
Figure 16A:
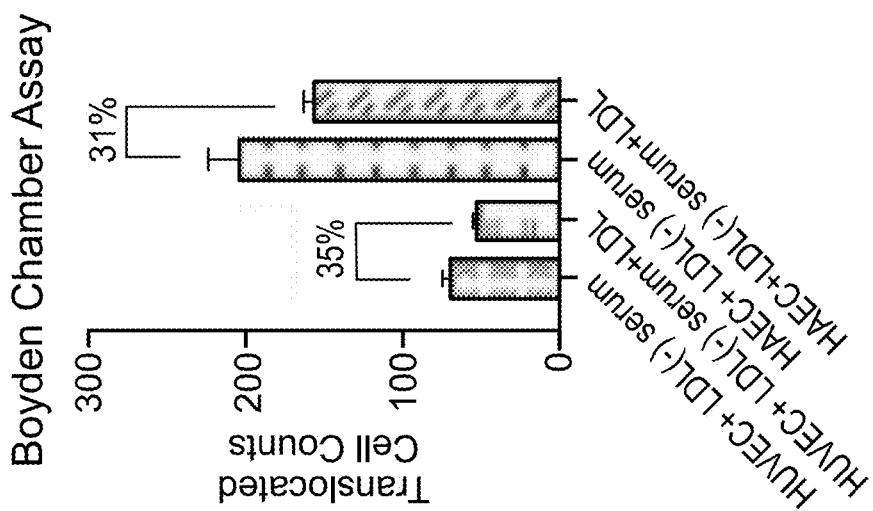

FIGS. 16A-B illustrates that LDL suppresses endothelial cell migration. HUVEC or HAEC migration assays were carried out in a Boyden Chamber in either LDL depleted serum (LDL(−)) or LDL(−) serum supplemented with LDL. All assays were performed in triplicate, measuring the number of transwell transmigrated cells, and standard deviations of the data were calculated. Addition of LDL to LDL(−) serum resulted in decreased migration of either HUVEC or HAEC. B. Migration was assessed by endothelial wound assays. Confluent endothelial monolayers were wounded with a 10 µl pipet tip. The wound was washed once with serum free media followed by incubation with media containing either LDL (10 µg/ml); 1% LDL-depleted serum or 1% LDL-depleted serum supplemented with 10 µg/ml of LDL. Cells under indicated treatment were imaged by time-lapse video microscopy. To calculate the cell migration rate, the wound area was determined prior and after completion of the experiment (8 hours). The graph represents four independent experiments in triplicates. Bars showed standard deviation. P=0.03. C, HUVECs were incubated with either 20% LPDS or 20% LPDS supplemented with LDL 10 µg/ml or 25 Vg/ml for indicated periods. The number of cells was then determined using the MTT cell growth assay. HUVEC proliferation is not affected by addition of LDL to LPDS medium.

DESCRIPTION OF SPECIFIC EMBODIMENTS OF THE INVENTION

The present invention, in some embodiments thereof, relates to methods of regulating angiogenesis by up or down regulation of Apolipoprotein B (apoB).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Despite the clear major contribution of hyperlipidemia to the prevalence of cardiovascular disease in the developed world, the direct effects of lipoproteins on endothelial cells have so far remained obscure and controversial.

The present inventors have now discovered a novel mechanism of vessel growth modulation by lipoprotein availability. Using novel genetic mutants, morpholino knockdown, and xenografts to manipulate lipoprotein levels in zebrafish, in combination with hyperlipidemic mice and cultured endothelial cells, the present inventors have demonstrated that apoB-lipoproteins negatively regulate angiogenesis (FIGS. 1A-Q).

Further the present inventors have provided mechanistic data highlighting VEGFR1, which acts as a decoy receptor for VEGF, as a key mediator of the endothelial response to lipoproteins (FIGS. 3A-P).

Finally the present inventors have shown that the apoB protein particle, but not the lipid moieties within apoB-lipoproteins, plays a major role in triggering the vascular response (FIGS. 4H-K).

Taken together, these findings define an important new pathway controlling the angiogenic switch, and open new avenues for the treatment of lipoprotein-related vascular disorders.

Thus, according to one aspect of the present invention, there is provided a method of treating an angiogenesis related disease or disorder in a subject in need thereof, the method comprising administering to the subject a therapeutically effective amount of an agent which regulates an amount of apolipoprotein B (ApoB), and/or an ability of ApoB to transcriptionally regulate vascular endothelial growth factor receptor 1 (VEGFR1), thereby treating the angiogenesis related disease.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein the term "subject" refers to any (e.g., mammalian) subject, preferably a human subject.

As used herein, the term "angiogenesis" refers to the generation of new blood vessels into a tissue or organ. Under normal physiological conditions, humans or animals only undergo angiogenesis in very specific restricted situations. For example, angiogenesis is normally observed in wound healing, fetal and embryonal development and formation of the corpus luteum, endometrium and placenta. The control of angiogenesis is a highly regulated system of angiogenic stimulators and inhibitors. The control of angiogenesis has been found to be altered in certain disease states and, in many cases, the pathological damage associated with the disease is related to the uncontrolled angiogenesis.

Angiogenesis-related diseases include, but are not limited to, inflammatory, autoimmune, and infectious diseases; angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; eczema; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; wound granulation; intestinal adhesions, atherosclerosis, scleroderma, wound healing, ischemic stroke, ischemic heart disease, gastrointestinal lesions, warts, and hypertrophic scars (i.e., keloids). The disease may have angiogenesis as a pathologic consequence such as cat scratch disease (*Rochele minalia quintosa*), ulcers (*Helobacter pylori*), tuberculosis, and leprosy.

Other examples of cancer for which the ApoB related agent may be administered according to this aspect of the present invention include, but are not limited to, adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma; meningioma; multiple endocrine neoplasia; myeloid malignancy, predisposition to; myxosarcoma, neuroblastoma; osteosarcoma; ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

As used herein, the phrase "down-regulating angiogenesis" refers to either slowing down or stopping the angiogenic process, which leads to formation of new blood vessels. The phrase "upregulating angiogenesis" refers to enhancing the expression of a dormant or minimally-functioning endothelial cell angiogenesis activator.

The term "Apolipoprotein B" or "ApoB", Swiss-Prot number P04114, refers to at least an active portion of ApoB (i.e., a portion having ApoB activity), which is the main apolipoprotein of chylomicrons and low density lipoproteins (LDL).

As used herein the phrase "ApoB activity" refers to at least the transcriptional activity of ApoB i.e., the ability of ApoB to up-regulate transcription of the target gene—VEGFR1. The transcriptional activity may be a direct activity on the VEGFR1 gene or a non-direct activity via an intermediate molecule/molecules. According to one embodiment, the ApoB comprises an amino acid sequence of a functional DNA binding domain.

ApoB may be found in the plasma in 2 main forms: apoB48 and apoB 100, which are synthesized in the intestine and liver, respectively, due to an organ-specific stop codon. ApoB48 contains 2,152 residues compared to 4,535 residues in apoB100. Cloning and characterization of APOB is described by, e.g., Glickman et al., PNAS USA 83:5296-5300 (1986); Chen et al., J. Biol. Chem. 261: 2918-12921 (1986); and Hospattankar et al., J. Biol. Chem. 261:9102-9104 (1986).

APOB sequences are set forth in, e.g., GenBank Accession Nos. NM_000384 and additional sequences such as AB208846.1, AJ399514.1 AK290844.1, BC051278.1, HM487065.1, J02610.1, K03175.1, M10374.1, M12413.1, M12480.1, M12681.1, M14081.1, M14162.1, M15421.1, M17367.1, M17779.1, M18036.1, M18471.1, M19734.1, M31030.1, M36676.1, X03045.1, X03324.1, X03325.1, X03326.1, X04506.1 and X04714.1.

The term "Vascular endothelial growth factor receptor 1" or "VEGFR1" refers to the receptor tyrosine kinases (RTKs) which contains an extracellular ligand-binding region with seven immunoglobulin (Ig)-like domains, a transmembrane segment, and a tyrosine kinase (TK) domain within the cytoplasmic domain. This protein binds to VEGFR-A, VEGFR-B and placental growth factor and plays an important role in angiogenesis and vasculogenesis. VEGFR1 may be encoded by any of the following four alternative transcripts: NM_001159920.1, NM_001160030.1, NM_001160031.1, or NM_002019.4.

Agents which increase the amount of ApoB include agents which are capable of increasing the transcription (for example a transcription factor known to interact with the 5' untranslated region of ApoB) of ApoB, the translation of ApoB or the stability of ApoB. Additionally, the agent which increases the amount of ApoB, may be a polynucleotide which encodes ApoB, the protein itself or an active peptide thereof.

As mentioned, the present invention also contemplates agents which are capable of increasing the ability of ApoB to transcriptionally upregulate VEGFR1 for decreasing angiogenesis. Such agents may act downstream of ApoB in order to induce transcription of VEGFR1.

All of the above described agents are useful for treating diseases where a decrease of angiogenesis is required. Such diseases include, but are not limited to cancer, arthritis, rheumatoid arthritis, atherosclerotic plaques, corneal graft neovascularization, hypertrophic or keloid scars, proliferative retinopathy, diabetic retinopathy, macular degeneration, granulation, neovascular glaucoma and uveitis.

Preferably the ApoB polypeptide (or the polynucleotide which encodes the ApoB polypeptide) which is administered to the subject is (or encodes a protein that is) at least 50% homologous, more preferably at least 60% homologous, more preferably at least 70% homologous, more preferably at least 80% homologous, and most preferably at least 90% homologous to the polypeptide sequence as set forth in SEQ ID NO:34 as determined using BlastP software of the National Center of Biotechnology Information (NCBI) using default parameters) comprising ApoB activity. The homolog may also refer to a deletion, insertion, or substitution variant, including an amino acid substitution, thereof and biologically active polypeptide fragments thereof.

Recombinant techniques are typically used to generate the ApoB polypeptides of the present invention. These techniques may be preferred due to the number of amino acids in ApoB polypeptides and the large amounts required thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce an expression vector for the expression of the ApoB of the present invention, a polynucleotide encoding the ApoB of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the ApoB of the present invention in the host cells.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the ApoB of the present invention, as well as some intronic sequences interposing there between. The intronic sequences can be of any source, including of other genes, and typically will include conserved splicing signal sequences. Such intronic sequences may further include cis acting expression regulatory elements.

As mentioned hereinabove, polynucleotide sequences of the present invention are inserted into expression vectors (i.e., a nucleic acid construct) to enable expression of the recombinant ApoB. The expression vector of the present invention may include additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

A variety of prokaryotic or eukaryotic cells can be used as host-expression systems to express the ApoBs of the present invention. These include, but are not limited to, microorganisms, such as bacteria transformed with a recombinant bacteriophage DNA, plasmid DNA or cosmid DNA expression vector containing the ApoB coding sequence; yeast transformed with recombinant yeast expression vectors containing the ApoB coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the ApoB coding sequence.

Other than containing the necessary elements for the transcription and translation of the inserted coding sequence (encoding the ApoB), the expression construct of the present invention can also include sequences engineered to optimize stability, production, purification, yield or activity of the expressed ApoB.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant peptide. Effective culture conditions include, but are not limited to, effective media, bioreactor, temperature, pH and oxygen conditions that permit protein production. An effective medium refers to any medium in which a cell is cultured to produce the recombinant ApoB of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Depending on the vector and host system used for production, resultant ApoB of the present invention may either remain within the recombinant cell, secreted into the fermentation medium, secreted into a space between two cellular membranes, such as the periplasmic space in E. coli; or retained on the outer surface of a cell or viral membrane.

Following a predetermined time in culture, recovery of the recombinant ApoB is effected.

The phrase "recovering the recombinant ApoB" used herein refers to collecting the whole fermentation medium containing the ApoB and need not imply additional steps of separation or purification.

Thus, the ApoB polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode an ApoB fused to a cleavable moiety. Such a fusion protein can be designed so that the ApoB can be readily isolated by affinity chromatography; e.g., by immobilization on a column specific for the cleavable moiety. Where a cleavage site is engineered between the ApoB and the cleavable moiety, the ApoB can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The ApoB of the present invention is preferably retrieved in "substantially pure" form.

As used herein, the phrase "substantially pure" refers to a purity that allows for the effective use of the ApoB in the applications described herein.

In addition to being synthesizable in host cells, the ApoB of the present invention can also be synthesized using in vitro expression systems. These methods are well known in the art and the components of the system are commercially available.

As mentioned, the ApoB may be administered to the subject in need thereof as polynucleotides where they are expressed in vivo i.e. gene therapy.

The phrase "gene therapy" as used herein refers to the transfer of genetic material (e.g. DNA or RNA) of interest into a host to treat or prevent a genetic or acquired disease or condition or phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ. The cells may be autologous or non-autologous to the subject. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

In in vivo gene therapy, target cells are not removed from the subject rather the genetic material to be transferred is introduced into the cells of the recipient organism in situ, that is within the recipient. These genetically altered cells have been shown to express the transfected genetic material in situ.

To confer specificity, preferably the nucleic acid constructs used to express the ApoB of the present invention comprise cell-specific promoter sequence elements.

Recombinant viral vectors are useful for in vivo expression of the ApoB of the present invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As mentioned, the present invention also contemplates agents which are capable of decreasing an amount of ApoB for enhancing angiogenesis. Such agents are useful for treating diseases such as in atherosclerosis induced coronary artery blockage (e.g., angina pectoris), in necrotic damage following accidental injury or surgery, or in gastrointestinal lesions such as ulcers.

Following is a list of agents capable of downregulating expression of ApoB.

One example, of an agent capable of downregulating ApoB is an antibody or antibody fragment capable of specifically binding thereto. Preferably, the antibody specifically binds at least one epitope of ApoB. As used herein, the term "epitope" refers to any antigenic determinant on an antigen to which the paratope of an antibody binds.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Downregulation of ApoB can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., ApoB) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex.

Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The invention according to some embodiments thereof also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with some embodiments of the invention can be effected as follows. First, the selected mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (wwwdotambiondotcom/techlib/tn/91/912dothtml).

Second, potential target sites are compared to an appropriate genomic database (e.g., human, mouse, rat etc.) using any sequence alignment software, such as the BLAST software available from the NCBI server (wwwdotncbidotnlmdotnihdotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a "cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIsl, TAT(48-60), pVEC, MTS, and MAP.

Another agent capable of downregulating ApoB is a DNAzyme molecule capable of specifically cleaving an mRNA transcript or DNA sequence of the SLUG. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl. Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther wwwdotasgtdotorg). In another application, DNAzymes complementary to bcr-ab1 oncogenes were successful in inhibiting the oncogenes expression in leukemia cells, and lessening relapse rates in autologous bone marrow transplant in cases of CML and ALL.

Downregulation of ApoB can also be effected by using an antisense polynucleotide capable of specifically hybridizing with an mRNA transcript encoding ApoB.

Another agent capable of downregulating ApoB is a ribozyme molecule capable of specifically cleaving an mRNA transcript encoding ApoB. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications.

An additional method of regulating the expression of ApoB in cells is via triplex forming oligonuclotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science,1989;245:725-730; Moser, H. E., et al., Science,1987;238:645-630; Beal, P. A., et al, Science,1992;251: 1360-1363; Cooney, M., et al., Science, 1988;241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003;112:487-94).

In general, the triplex-forming oligonucleotide has the sequence correspondence:

```
oligo     3'--A     G     G     T
duplex    5'--A     G     C     T
duplex    3'--T     C     G     A
```

However, it has been shown that the A-AT and G-GC triplets have the greatest triple helical stability (Reither and Jeltsch, BMC Biochem, 2002, September 12, Epub). The same authors have demonstrated that TFOs designed according to the A-AT and G-GC rule do not form non-specific triplexes, indicating that the triplex formation is indeed sequence specific.

Thus for any given sequence in the ApoB regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

The agents of the present invention can be provided to the individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the active agent (e.g. polypeptide, polynucleotide or antibody preparation), which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmuc o s al administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Since the present inventors have shown that ApoB regulates VEGFR1 transcription, the present inventors contemplate identification of additional agents other that those listed herein above for the treatment of angiogenesis related disorders.

Thus, according to another aspect of the present invention, there is provided a method of identifying an agent which regulates angiogenesis comprising:

(a) introducing the agent into a cell;

(b) analyzing VEGFR1 transcription in the cell; and (c) identifying the agent capable of regulating ApoB-dependent VEGFR1 transcription in the cell, thereby selecting the agent which regulates angiogenesis.

As used herein, the phrase "ApoB-dependent VEGFR1 transcription" refers to the transcription of VEGFR1 which requires the presence of a functional ApoB. The present inventors postulate that ApoB may up-regulate transcription either by binding directly to the promoter region or alternatively by binding to another polypeptide which is capable of binding to the VEGFR1 promoter region.

Agents that are able to up-regulate ApoB dependent transcription of VEGFR1 include agents that increase the activity (i.e. transcriptional activity) or amount of endogenous ApoB and also agents that are able to mimic (i.e. compete with) ApoB's ability to enhance VEGFR1 transcription.

Any type of agent may be identified according to the method of the present invention, including but not limited to polynucleotide agents and polypeptide agents. Candidate agents encompass numerous chemical classes, such as organic molecules, e.g. small organic compounds having a molecular weight of more than 50 and less than about 2,500 daltons. Candidate agents typically comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, pheromones, purines, pyrimidines, derivatives, structural analogs or combinations thereof.

Candidate agents may be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

According to one embodiment, the agent that is capable of up-regulating ApoB dependent transcription is a peptide agent. An exemplary agent of the present invention is one that comprises a ApoB (i.e. a ApoB derived peptide).

The term "peptide" as used herein refers to a polymer of natural or synthetic amino acids, encompassing native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides even more stable while in a body or more capable of penetrating into cells.

Candidate peptide sequences may be screened by determining if there is an interaction between them and the VEGFR1 promoter. Exemplary methods for such screening include EMSA (electromobility shift assay) and chromatin precipitation. Such methods are known to one skilled in the art.

Alternatively or additionally, the candidate peptides may be screened for regulatory activity of VEGFR1 transcription. An exemplary method for analyzing such regulatory activity comprises transfecting a polynucleotide encoding the promoter region of VEGFR1 (i.e. an exogenous VEGFR1 promoter) linked to a detectable protein (i.e. reporter protein) into a cell—i.e. a reporter based assay. The method further comprises introducing the candidate peptide agents into the cell (e.g. by transfection of an expression vector encoding the agent) and detecting the detectable protein whereby the amount of the detectable protein reflects the transcriptional activity of the promoter. It will be appreciated that the polynucleotide sequence of any protein that may be readily detected may be transcriptionally linked to the VEGFR1 promoter. Thus for example, the protein may be a phosphorescent protein such as luciferase, a fluorescent protein such as green fluorescent protein, a chemiluminescent protein or may be a non-directly detectable protein for which an antibody is available for detection thereof. Cells for analyzing transcriptional activity are further described hereinbelow.

It will be appreciated that transcriptional activity of endogenous VEGFR1 may also be analyzed with VEGFR1 being detected using a detectable agent such as an antibody.

Once the minimal amino acid sequence of ApoB is identified that is capable of transcriptionally activating VEGFR1, other peptides may be synthesized (comprising conservative or non-conservative substitutions) in order to "tweak the system" and generate ApoB-derived peptides with improved characteristics i.e. comprising an enhanced transcriptional activity.

Another way of identifying agents that regulate angiogenesis is by performing a reporter assay wherein the 3' untranslated region (UTR) (i.e. promoter) of ApoB is operatively attached to a reporter molecule and introduced into a cell together with the candidate agent, wherein a change in the amount of the reporter molecule is indicative of the agent which regulates angiogenesis.

Since the present inventors have shown that ApoB decreases angiogenesis, the present inventors further contemplate that analysis of the level of ApoB may be used to diagnose whether a cancer is metastatic or not. More specifically, the present inventors propose that a decrease in the level of ApoB compared to a control subject is indicative that the cancer is metastatic.

Thus, according to another aspect of the present invention there is provided a method of identifying a metastasized cancer in a subject in need thereof, comprising determining the level of ApoB in a fluid sample of the subject, wherein an up-regulation of the level of the ApoB compared to the level of ApoB in the fluid sample of a control subject, is indicative of a metastasized cancer.

Examples of fluid samples which may be analyzed for ApoB include, but are not limited to blood, plasma, saliva and urine.

The level of ApoB may be analyzed on the protein level (e.g. by using antibodies) or the polynucleotide level (i.e. RNA level).

Methods of Detecting the Expression Level of RNA

The expression level of ApoB RNA can be determined using methods known in the arts, including for example Northern Blot analysis, RT-PCR analysis, RNA in situ hybridization, in situ RT-PCR, DNA microarrays/DNA chips, oligonucleotide microarray.

Methods of Detecting Expression and/or Activity of Proteins

Expression and/or activity level of proteins expressed in the cells of the cultures of some embodiments of the invention can be determined using methods known in the arts including for example Enzyme linked immunosorbent assay (ELISA), Western blot, Radioimmunoassay, Fluorescence activated cell sorting (FACS), Immunohistochemical analysis, In situ activity assay and In vitro activity assays.

Comparison with control subjects may be effected on healthy subjects or cancer patients, wherein the cancer is known not to be metastatic.

Typically, the ApoB level is at least 1.5 times, at least two times, at least 4 times, at least 5 times the amount in control subjects in order to indicate metastasis.

As used herein the term "about" refers to ±10%.

The terms "comprises", "comprising", "includes", "including", "having" and their conjugates mean "including but not limited to".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Zebrafish Husbandry and Injection: Zebrafish were raised by standard methods. The Tg(fli1:EGFP)$^{y1}$, Tg(fli1:nEGFP)$^{y7}$ [Yaniv et al., Nat Med 12, 711-716 (2006)] and Tg(flt1:YFP)$^{hu4624}$ [Hogan et al., Nat Genet 41, 396-398 (2009)] lines were previously derived. MOs and DNA were injected as further described below.

Cloning of mtp and Rescue of the Mutant Phenotype: The full-length coding sequence of zebrafish mtp was amplified by PCR from WT cDNA and cloned into a pCSDest vector [Villefranc et al., Dev Dyn 236, 3077-3087 (2007)] as further described herein below. mtp mRNA was synthesized with mMessage mMachine kit (Ambion) and injected at a concentration of 232 pg per embryo into the 1 cell stage cytoplasm or into the YSL at dome stage (approximately at 4 hpf).

Microangiography and Cell Transplants: 10 μM Atorvastatin (Sigma), 1 ug/μl DiI-LDL (Invitrogen), 6 μg/ml $C_6$ in 0.5% BSA Fatty Acid Free (Sigma A8806) and Human Apolipoprotein B-100 (A50220H Meridian Life Science) in 0.5% BSA Fatty Acid Free (Sigma A8806) microangiography was performed at 2.5 dpf as described [Isogai et al., Dev Biol 230, 278-301 (2001)]. HEK293 cells co-transfected with Huh7MTP+apoB34 (see herein below) or un-transfected control cells were transplanted into the perivitelline space of one side of the yolk of 2.5 dpf stl; Tg(fli1:EGFP)$^{y1}$ mutant or WT embryos, ventral to the developing SIVs [Nicoll et al., J Cell Mol Med (2008)].

In Situ Hybridization, Oil Red 0, and Alkaline Phosphatase (AP) Staining: Embryos were fixed overnight in 4% PFA and processed for AP staining [Habeck et al., Curr Biol 12, 1405-1412 (2002)], Oil Red 0 staining [Schlegel et al., Biochemistry 45, 15179-15187 (2006)], or whole-mount in situ hybridization using antisense mRNA probes for vegfr1, vegfr2, vegfr3 and VeCad as described [Pham et al., Dev Biol 303, 772-783 (2007)].

Zebrafish Western Blot: 3 dpf zebrafish embryos were processed for Western Blot as described [Yaniv et al., Nat Med 12, 711-716 (2006)]. VEGFR1 was detected using a 1:500 dilution of a chick polyclonal serum (Ayes Labs). Blots were then reblocked by standard protocols and probed with a 1:5000 dilution of α-tubulin antibody (Sigma).

Mice and Immunofluorescence: ApoE and LDLR null mice (Jackson Laboratory) and their WT C57B1/6 controls were handled according to the Weizmann Institute Animal Care and Use Committee. All the analyses were performed between 8-38 weeks (n=3 for each group) on mice fed with normal chow diet. Following anesthesia, aortas were dissected and frozen for further PCR analyses or fixed for 3 hours in 4% Para formaldehyde, equilibrated for 36 hours in 30% sucrose in PBS-T, embedded in OCT and frozen at −80° C. Slides of 7 μm sections were fixed in cold methanol, blocked with BSA and goat serum and stained overnight with anti-CD31 (BD 550274) and anti-VEGFR1 (Abcam AB2350) antibodies. Slides were then incubated for 2 hours with Cy3 anti-rabbit and Cy2 anti-rat antibodies (Jackson), stained with DAPI (10 mM Inno-Train Diagnostik) and mounted in fluorescent mounting medium. Images were captured using a Zeiss LSM780 confocal microscope.

Microscopy and Imaging: Zebrafish embryos used for imaging or in situ hybridization were treated with 0.00 3% phenylthiourea from 8hpf to inhibit melanin pigment formation. Confocal imaging was performed using a FVIOOO Olympus imaging system or Zeiss LSM780 upright confocal microscope equipped with ×20 NA 1.0 lens.

Injection of Zebrafish Embryos: The mtp [Schlegel, A. & Stainier, D. Y. Biochemistry 45, 15179-15187 (2006)], apoCII [Pickart, M. A., et al. PLoS One 1, e104 (2006);

```
vegfr1
                                         (SEQ ID NO: 1)
5'-ATATCGAACATTCTCTTGGTCTTGC-3', apoB
                                         (SEQ ID NO: 2)
5'-CAACTTAGTGTCCATTTTTATCGGC-3'
and apoA1
                                         (SEQ ID NO: 3)
5'-TCAGTGCAAGAGCCACGAATTTCAT-3,
```

MOs (Gene-Tools) were resuspended and injected at concentrations from 5-20 ng/embryo.

pCS2vegfr1CDS mRNA (1200 ng/embryo) and pCS2mtpCDSmRNA (232 ng/embryo) were injected at the 1 cell stage or at dome stage, respectively.

Positional Cloning: Generation of map-cross lines, bulk segregant analyses, genomic DNA isolation and PCR were performed as described [Roman et al., Development 129, 3009-3019 (2002). Polymorphism analyses and sequence comparisons were performed using SeqMan alignment software (DNASTAR, Inc.).

Generation of pCS2mtpCDS and pCS2vegfr1CDS: The following primers were used to amplify the full-length coding sequences of zebrafish mtp and vegfr1:

```
mtp:
                                         (SEQ ID NO: 4)
5'-ATGATGCCGGTTGCCGGACT-3'
and (SEQ ID NO: 5)
5'-TTACCAGGCCGGCTCAAAGA-3' vegfr1:
                                         (SEQ ID NO: 6)
5'-GACCAAGAGAATGTTCGATATATTATTTGTG 3'
and (SEQ ID NO: 7)
5'-TTAGAAACTGGGGTAAAGAAGATCGCCTTC-3'.
```

Following TOPO (Invitrogen) cloning and sequencing, a Gateway (Invitrogen) compatible middle Entry clone was generated by BP recombination. The mtp and vegfr1 coding sequences were then transferred into a pCSDest vector 5 using a Gateway LR reaction (Invitrogen) to give pCSmtpCDS and pCSvegfr1CDS. Following linearization with NotI, the vectors were used as templates for mRNA synthesis.

HEK293 Transfection: 50% confluent HEK293 cells were co-transfected with 1 µg each of ApoB34 and Huh7MTP for 6 hours, using fugene 6 (Roche). Following transfection, cells were labeled with Cell tracker orange CMRA (Invitrogen) for 45 minutes and grown overnight in serum supplemented DMEM media.

Cloning of Huh7MTP: Huh? (human hepatoma) cell RNA was subjected to RT-PCR using

```
                                         (SEQ ID NO: 8)
5'-AGAAAGCTTGCTGGTCAATATGATTCTTCTTGC-3'
and (SEQ ID NO: 9)
5'-AGATCTAGAATCACAGGTCAGTTTCAAAACCATCC-3' primers.
```

The PCR product was cloned into pCMV5, sequenced and found to be identical to a human MTP cDNA (Locus EAX06106; accession CH471057.1). For functional characterization of Huh7MTP, see FIG. 14A-B.

Quantitative Analysis of HEK293 Cell Transplants: 3.5 dpf embryos, successfully transplanted with fluorescent red cells adjacent to green fluorescent endothelial cells were imaged and phenotypic quantitation was performed. The total length of the interface between endothelial and transplanted cells (see FIG. 15), as well as the total length of overlapping between the two cell populations (see FIG. 15) were traced and measured. The ratio r=L2/(L1+L2) was used to measure the ability of endothelial cells to migrate on top of ApoB secreting cells. The ratios were computed for three transplanted animals per treatment (transfected and untransfected HEK293 cells), and were compared using t-test.

RNA Isolation from Mouse Aortic Tissue and RT-PCR Analyses: Dissected Aortas from C57B1/6 and ApoE null mice (500 mg tissue per sample) were homogenized in Trizol and processed for RNA isolation and semi-quantitative PCR. For all samples, cDNA was generated from equal amounts of RNA (600 ng). Primers to measure relative changes in vegfr1 mRNA transcripts were:

```
                                         (SEQ ID NO: 10)
5'GGCCCGGGATATTTATAAGAAC-3'
and (SEQ ID NO: 11)
5'-CCATCCATTTTAGGGGAAGTC-3'.
```

Expression levels were standardized to the primer set specific for β2-microglobulin:

```
                                         (SEQ ID NO: 12)
5'-GTCTCGATCCCAGTAGACGG-3'
and (SEQ ID NO: 13)
5'-TGGTGCTTGTCTCACTGACC-3'3'.
```

Quantitative analyses were performed using ImageJ.

Total RNA Isolation from Zebrafish Embryos, Semi Quantitative and Quantitative Real-Time PCR Analysis: 30-60 WT or mtp MO injected embryos were homogenized in Trizol (Invitrogen) and processed for RNA extraction following standard procedures. After precipitation, RNA was treated with DNase using the DNA free kit (Ambion) to eliminate genomic DNA.

1 µg of total RNA per reaction was reverse transcribed using the ThermoScript RT-PCR kit (Invitrogen). In yfp measurement experiments, RNeasy mini kit (QIAGENE) was used for RNA extraction and 1 µg of total RNA per reaction was reverse transcribed using High Capacity cDNA Reverse Transcription Kit (Applied Biosystem).

Primers to measure relative changes in mRNA transcripts were as follows:

```
vegfr1:
                                   (SEQ ID NO: 14)
5'TGGTCATATGGAGTCCTGCTC-3'3'
and
                                   (SEQ ID NO: 15)
5'-CATGTTGAGTCCTGGGTATGG-3'3' vegfr2:
                                   (SEQ ID NO: 16)
5'-CTGGTGGAGAGGCTAGGAGA-3'
and
                                   (SEQ ID NO: 17)
5'-TGATCGGGATGTAGTGCTTTC-3' vegfr3:
                                   (SEQ ID NO: 18)
5'-TAACCAACCCCTCCATCAGA-3'
and
                                   (SEQ ID NO: 19)
5'-CTGAATGCTGAGAGTCCGATT-3' cdh5:
                                   (SEQ ID NO: 20)
5'-GCACATGAAGATGTGTTGAATG-3'
and
                                   (SEQ ID NO: 21)
5'-TGGTTAGTTCTGGTGCATTGTC-3' fli1:
                                   (SEQ ID NO: 22)
5'-CCATCTCACGGCTGACCAGT-3'
and
                                   (SEQ ID NO: 23)
5'-GACAGCGCACACAACCAC-3' yfp:
                                   (SEQ ID NO: 24)
5'-CACATGAAGCAGCACGACTT-3'
and
                                   (SEQ ID NO: 25)
5'-GGTCTTGTAGTTGCCGTCGT-3'.
```

Expression levels were standardized to the primer set specific for ef1α and β actin:

```
ef1a:
                                   (SEQ ID NO: 26)
5'-CCTCTTTCTGTTACCTGGCAAA-3'
and
                                   (SEQ ID NO: 27)
5'-CTTTTCCTTTCCCATGATTGA-3'

β actin:
                                   (SEQ ID NO: 28)
5'-TGACAGGATGCAGAAGGAGA-3'
and
                                   (SEQ ID NO: 29)
5'-GCCTCCGATCCAGACAGAGT-3'.
```

Reactions were run in 96-well plates in a LightCycler 480 Real-Time PCR System (Roche) or in Step One Plus real time PCR system (Applied Biosystem) and results were analyzed using built-in software. Measurements were conducted in duplicates.

For semi quantitative real-time PCR, primers used to measure relative changes in mtp mRNA transcripts were

```
                                   (SEQ ID NO: 30)
5'-CCGTCTTACATGGAGGTGAA-3'
and
                                   (SEQ ID NO: 31)
5'-CGGACATGGAGAACATCTTG-3.
```

Expression levels were standardized to the primer set specific for

```
β actin:
                                   (SEQ ID NO: 32)
5'-CAGCTAGTGCGAATATCATCT-3'
and
                                   (SEQ ID NO: 33)
5'-TTTCTGTCCCATACCAACC-3'.
```

Cell Cultures and Reagents: Human aortic endothelial cells (HAECs) and human umbilical vein endothelial cells (HUVECs) (VEC Technologies and Promo Cells) were cultured in complete MCDB 131 medium (VEC Technologies) or in M199 medium supplemented with ECGS (Zotal).

Boyden Chamber Assays: HUVECs or HAECs (50,000/well) were seeded on the top well of a Boyden Chamber (5 μm pore size) and cultured overnight at 37° C. and 5% $CO_2$. Subsequently, the bottom wells were filled with either LDL (−) serum, or LDL(−) serum supplemented with 10 μg/ml LDL for overnight incubation. After incubation was completed, endothelial cells (ECs) that remained on the upper side of the membrane were scrapped off with a cotton swab. Endothelial cells that transmigrated were stained with DAPI and imaged using fluorescent microscopy. Positive nuclei were counted in 3 random image fields. Three individual experiments were conducted and the averages were used to generate the bar graph.

Wound Healing Assay: HUVECs exposed to either siRNA control (non-targeting) or siRNA for VEGFR1 were plated to confluency for wound assays. A 200 μm wound was inflicted in both groups and each was treated with either LDL or vehicle. Migration of cells was recorded for 24 hrs (note proliferation cycle of these cells ranges from 36 to 48 hrs). Four wells per experimental group were measured. Results were normalized to control and expressed as migration area over control.

Small Interfering RNA: siRNA reagents were obtained from Dharmacon Research, Inc (Chicago, Ill.). Endothelial cells at 90% confluency were transfected with DharmaFECT transfection reagents in the absence of antibiotics. For transfection either VEGFR1 siRNA SMARTpool or non-targeting siRNA (siCONTROL) were used at 100 nmol/L following manufacturer's instructions. Efficiency of the siRNA was evaluated by standard Western blots against VEGFR1 and resulted in 78 to 85% reduction of VEGFR1 protein. Experiments on migration were conducted 48 hrs post-transfection.

MTT Proliferation Assay: HUVECs were plated in 96 well plates (coated with 0.2% gelatin) at a density of 2000 cells/well in 0.2 ml growing medium. After 24 hours the medium was washed and cells were incubated with either 20% LPDS, or 20% LPDS supplemented with LDL 10 or 25 μg/ml for indicated periods. The number of cells was then determined using the MTT cell growth assay. Briefly, MTT reagent (Sigma M5655) was added to the wells at a final concentration of 0.6 mg/ml, the cells were further incubated at 37° C. for 2 hours. The reaction was terminated by adding 100 μl/well of an extraction solution consisting of 20% SDS in a 50% DMF solution. Absorbance was read at 570 nm using an ELISA plate reader, after leaving the plates protected from light overnight.

Fatty Acids Feeding of Zebrafish Embryos: Dechorionized 24 hours post fertilization (hpf) embryos were incubated with 6 μg/ml short, intermediate or long chain fatty acid in a solution containing 0.1% BSA Fatty Acid Free (Sigma A8806) for 48 hours. Embryos were then fixed overnight in 4% PFA and processed for AP staining.

Triglyceride Content Measurements: Dechorionized 24 hpf embryos were incubated with 2 μCi/ml $^3$H Oleic Acid (Perkin Elmer NET289005MC) in a solution containing 0.1% BSA Fatty Acid Free (Sigma A8806) and 3 μg/ml oleic acid (Sigma O1383) for 48 hours. After deyolking, the embryos were homogenized in 1 ml cold methanol. Lipids were extracted following the method of Bligh and Dyer [Can J Biochem Physiol 37, 911-917 (1959)] adding ice cold chloroform and DDW. The lower chloroform phase was collected and evaporated under vacuum or $N_2$ and kept at -20° C. Lipids were developed on silica gel 60 TLC plates in a solvent system of Petroleum Ether: Diethyl Ether: Acetic Acid (80:20:1). Labeled lipids were visualized with autoradiography and spots corresponding to triglyceride standards (Sigma 17811) were scraped and quantified using liquid scintillation fluid. For HPLC, samples were lyophilized for 2 hours and 10 μl of pyridine and 80 μl of N-methyl-N-trimethylsilyl trifluoroacetamide were added to dry residue. The samples were then shaken vigorously for 30 seconds, and the mixture was transferred to a 2-ml autosampler glass vial with a 100-ml conical glass insert. After capping the vial, the reaction mixture was incubated at room temperature for at least 1 hour. For the GC-MS instrument and analytical parameters, CT split 1:25 mode was used. Cholesterol was identified by comparison of its retention time and mass spectrum to those generated for authentic standard analyzed in the same sequence. Relative quantification was performed using the reconstructed ion chromatogram generated from the characteristic cholesterol fragments: 329, 353, 368 and 458 Da.

FACS Sorting of ECs from Zebrafish Embryo: 3dpf Tg(fli1:EGFP)$^{y1}$ embryos were used for FACS sorting of GFP labeled endothelial cells. Single cell suspensions were prepared as described in Takada et al [Dev Dyn 239, 2041-2047 (2010)]. Sorting was performed at 4° C. in FACSAria cell sorter using a 70 μm nozzle. GFP$^+$ and GFP$^-$ cells were separately collected in 1 ml FCS. Sorted cells were washed with PBS and centrifuged at 300 g at 4° C. for 5 min twice. The cell pellet was suspended in 1 ml Trizol for RNA extraction.

HUVEC Immunoblotting: HUVECs were lysed for 30 minutes in mRIPA buffer. Proteins were separated by SDS-PAGE and transferred to nylon membranes (Whatman). Membranes were then probed with VEGFR2 (Cell Signaling) or VEGFR1 antibodies (R&D) and detected by enhanced chemiluminescence (Thermo Fisher Scientific).

Example 1

Stl, a Zebrafish Mutant Exhibiting Excessive Angiogenesis

The present inventors identified stalactite (stl), a zebrafish mutant displaying excessive sprouting angiogenesis, in a Tg(fli-EGFP)$^{Y1}$ transgenic-based forward-genetic screen for vascular-specific mutations. stl mutants display ectopic angiogenic segments that extend ventrally from the subintestinal (SI) plexus (FIGS. 1A-D), a vascular bed that initially forms bilaterally over the dorsal-lateral aspect of the large zebrafish yolk cell (FIG. 5). Quantitative analysis (FIG. 6) reveals large increases in both the number and length of ventral SI sprouts in stl mutants (FIG. 1E) when compared to wild type siblings. Increased angiogenic branching is also observed in the dorsal part of the intersegmental vessels (ISVs) at slightly later stages of development (FIGS. 1F-H). Endothelial nuclei were counted in the yolk area of wild type and stl;Tg(fli:nEGFP)$^{y7}$ embryos to determine whether formation of ectopic sprouts in stl mutants involved overproliferation of endothelial cells. Total SI endothelial cell number is increased by 42% in stl mutants, with excess cells found exclusively in the ectopic ventral sprouts (FIGS. 1I-J). stl mutants also display defects in yolk absorption (FIG. 5) and the larvae die by approximately 6 days post fertilization (dpf).

In order to examine the molecular nature of the stl phenotype, the present inventors positionally cloned the defective locus. The mutation was genetically mapped to an interval in linkage group 1 (See FIG. 7 for details) containing the gene encoding microsomal triglyceride transfer protein (mtp). Sequence analysis of mtp cDNA from stl mutants and their phenotypically wild type siblings revealed a change in a conserved leucine (Leu475) residue to a proline (FIG. 7). MTP, an intraluminal protein found within the endoplasmic reticulum of liver and intestine, is required for assembly and secretion of proatherogenic-, apoB-containing lipoproteins such as chylomicrons, very low-density lipoproteins (VLDLs), and low-density lipoproteins (LDLs). Following their assembly as mature particles, apoB-lipoproteins are secreted to the blood and lymph stream by MTP. Even though the MTP/apoB lipoprotein pathway was originally thought to be unique to the liver and intestine, the demonstration that the murine yolk sac expresses mtp and that mice homozygous for an mtp gene disruption die at E10.5 underscores the importance of the synthesis and secretion of apoB-containing lipoproteins during early embryogenesis. The yolk syncytial layer (YSL) of the fish (the functional counterpart of the yolk sac of higher vertebrates) expresses mtp starting at the gastrula stage and forms apoB-related lipoproteins, which enter the circulatory system and deliver nutrient lipids to the tissues. As in mice and humans, fish mtp is involved in lipoprotein assembly in the YSL and is found later in the intestine and liver. In addition, zebrafish have structural and functional homologues of mammalian apoAI, apoCII, apoE, phospholipase A2 and lipoprotein lipase.

Four additional lines of evidence confirm that a mutation in mtp is responsible for the stl phenotype. First, injection of antisense morpholino oligonucleotides (MOs) against mtp [Schlegel et al., Biochemistry 45, 15179-15187 (2006)], reproducibly phenocopies the angiogenesis and yolk absorption phenotypes seen in stl mutants (FIG. 1K and FIG. 8A). Second, injection of mtp mRNA into stl mutants suppresses ectopic sprouting and RNA-rescued larvae survive for at least 10 dpf (FIG. 1L and FIG. 8B). Third, downregulation of apoB using apoB MOs leads to ectopic SIV branching, reminiscent of that displayed by stl mutants (FIGS. 8C-E). This pro-angiogenic response however, is not observed upon down-regulation of apoA1 (FIG. 8F). Finally, reduction of LDL levels in WT embryos using atorvastatin, efficiently phenocopied the excess angiogenesis phenotype of stl mutants (FIG. 1M-0). Altogether these results confirm the specificity of the MTP/apoB pathway in causing excess angiogenesis.

The restricted expression of the mtp transcript in the yolk syncytium, liver, and intestine, and the lack of vascular expression (FIG. 8G), strongly suggests that its role in vessel development is non-cell autonomous. To confirm this notion, the present inventors injected mtp mRNA into the yolk syncytium at dome stage. As the cytoplasmic bridges between the embryo and the yolk cell are closed by the 1000-cell stage, reagents injected into the yolk cell after this stage are restricted exclusively to the yolk syncytium. As expected for a YSL-specific defect, injection of mtp mRNA at dome stage yielded efficient rescue of the stl excess angiogenesis phenotype (FIG. 8B).

In humans, mutations in mtp are the proximal cause of abetalipoproteinemia, an autosomal recessive defect in the production of apoB-containing lipoproteins that results in a virtual absence of LDL in blood. To confirm that the effects of mtp downregulation on lipoprotein production and/or secretion are conserved in zebrafish, WT and stl mutant embryos were stained with Oil Red O (ORO). As seen in FIG. 1P, Q, stl mutants display a clear absence of lipids in the vasculature (FIG. 1$q$) when compared to WT siblings (FIG. 1P). To further confirm the lipoprotein-depletion phenotype, a more detailed lipid analysis was performed. Taking advantage of the fact that exogenously supplied-, radioactively-labeled fatty acids are properly processed by zebrafish larvae, and are found as expected in the triglycerides (TGs) fraction, thin layer chromatography (TLC) was performed to confirm that triglycerides are strongly reduced in stl mutants (FIG. 9). Same results were obtained when the levels of cholesterol were analyzed using gas chromatography-mass spectrometry (GC-MS) (See FIG. 9 for details).

Example 2

The Excess Angiogenesis Phenotype is not Caused by Global Lipid Starvation

To further characterize the effects of lipoproteins on angiogenesis in vivo, the present inventors generated a zebrafish model of lipoprotein overload in circulation by down-regulating the apoCII gene. ApoCII is a component of apoB-containing lipoproteins required for activation of the enzyme lipoprotein lipase (LPL) in blood capillaries. LPL activation leads to triglyceride hydrolysis, and to release of free fatty acids for use by cells. In humans, mutations in apoCII result in accumulation of unprocessed lipoproteins in circulation (hyperlipoproteinemia type IB and hypertriglyceridemia), and increased risk of early atherosclerosis. The present inventors reasoned that while morpholino knockdown of apo CII early in development would lead to a global reduction in lipid delivery, the endothelial cells of these morphants would nevertheless be exposed to elevated concentrations of plasma lipoproteins, mimicking the hyperlipidemia described in higher vertebrates. Injection of apoCII MOs into Tg(fli-EGFP)$^{y1}$ embryos did result in increased intravascular levels of lipoproteins as demonstrated by ORO staining at 4 dpf (FIG. 2A; compare with FIG. 1P,Q). This was accompanied by a significant reduction in TGs and cholesterol delivery to cells (FIG. 9B, C). In contrast to the excess angiogenesis phenotype displayed by stl mutants however, no ectopic SW sprouts were observed in apoCII (FIG. 2B-C) or lpl morphants (FIGS. 10A-D), confirming that global lipoprotein starvation per se does not lead to excessive angiogenesis. On the contrary, high lipoprotein levels in circulation resulted in a poorly developed vasculature characterized by short and partially lumenized ISVs (FIGS. 2D-F). These results are consistent with previous findings describing premature vascular disease [Connelly et al., J Clin Invest 80, 1597-1606 (1987)], and general endothelial dysfunction [Landmesser et al., Seminars in thrombosis and hemostasis 26, 529-537 (2000)] under hyperlipoproteinemic conditions in humans [Henry et al., The American journal of cardiology 72, 61C-64C (1993)].

To further demonstrate that the angiogenic phenotypes seen in stl and apoCII morphants result from a direct response of endothelial cells to lipoprotein levels, and not from alternative cues trigged by fatty acid depletion, the present inventors checked the ability of exogenously supplied fatty acids to restore a normal vasculature. Addition of short-, intermediate-, and long-chain fatty acids to the embryo media, did not rescue the vascular phenotypes in stl mutants (FIGS. 2G-K) or apoCII morphants (FIG. 2L, M, N and data not shown), even when applied at high concentrations (FIG. 11), confirming that the angiogenic phenotypes result from a direct response of endothelial cells to lipoprotein levels.

Example 3

Lipoprotein Levels Regulate VEGFR1 Expression

Figure 3B:
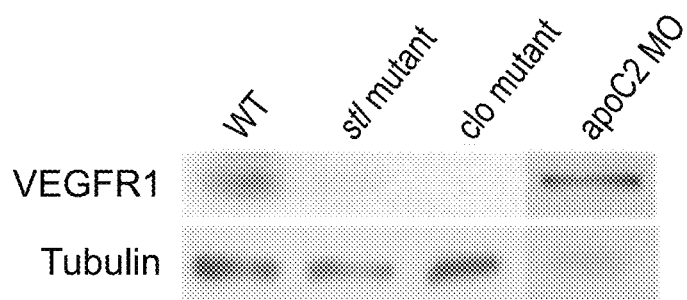
Figure 3C:
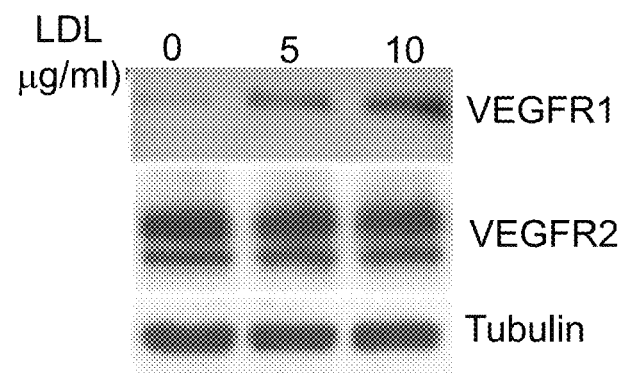

To elucidate the mechanisms underlying the effects of lipoproteins on vascular growth, the present inventors set out to identify the specific elements within endothelial cells on one hand, and apoB-lipoproteins on the other, responsible for the angiogenic phenotypes. They began by searching for endothelial specific candidates whose expression was affected by changes in lipoprotein levels. qRT-PCR (FIG. 3A) and in situ hybridization (FIG. 12) revealed dramatic reduction in vegfr1 mRNA in mtp MO-injected embryos at 24 hpf. This reduction was specific for vegfr1, since little change was detected in the levels of vegfr2, vegfr3, or other vascular genes (FIG. 3A, FIG. 12, and data not shown). VEGFR1 protein levels were also strongly reduced in stl mutants, but were significantly up-regulated in apoCII morphants, where endothelial cells face high concentrations of apoB-lipoproteins (FIG. 3B). Similar effects on VEGFR1 levels were observed in endothelial cells in vitro. Addition of LDL, the metabolic product of apoB-containing lipoproteins, to cultured HUVECs did not affect levels of VEGFR2, but elicited increases in VEGFR1 levels (FIG. 3C). Finally, hyperlipidemic apoE (FIGS. 3D-E, H) and LDL-R (FIGS. 3F-G) null mice also showed increased endothelial-specific VEGFR1 expression, confirming the conservation of this pathway among vertebrates.

Previous studies have shown that VEGFR1 plays an inhibitory role in angiogenesis, acting as a "sink" for VEGF ligand Hiratsuka, S., et al. Proceedings of the National Academy of Sciences of the United States of America 95, 9349-9354 (1998); Kearney, J. B., et al. Blood 99, 2397-2407 (2002); Chappell, J. C., et al., Developmental cell 17, 377-386 (2009). Downregulation of vegfr1 by ATG blocking morpholinos results in excess sprouting and branching from the SIV plexus, and trunk ISVs, reminiscent of those found in stl mutants (FIG. 13). The present inventors reasoned that if lipoprotein depletion promotes angiogenesis via downregulation of VEGFR1, it should be possible to rescue the pro-angiogenic phenotype of stl mutants by vegfr1 overexpression. Indeed, injection of vegfr1 mRNA into stl mutant embryos suppresses ectopic SIV sprouting (FIGS. 3I-K). Furthermore, siRNA-mediated downregulation of VEGFR1 (FIG. 3L) abolished the ability of cultured endothelial cells to respond to LDL levels in a Wound Healing assay (FIG. 3M).

The changes in vegfr1 mRNA levels observed in stl mutants (FIG. 3A) and apoE null mice (FIG. 3H) could result from either transcriptional regulation, or post-transcriptional modifications that alter RNA stability of the vegfr1 transcript. To distinguish between these two possibilities, the present inventors took advantage of a transgenic zebrafish reporter expressing YFP under the regulation of the vegfr1 promoter, which efficiently recapitulates the pattern of expression of the endogenous vegfr1 gene. It was hypothesized that if lipoproteins regulate vegfr1 mRNA expression at the transcriptional level, downregulation of mtp will result in a significant decrease in the levels of yfp mRNA. If in turn, vegfr1 downregulation involves alterations in its mRNA stability, the levels of yfp mRNA will remain unchanged upon mtp MOs injection. As seen in FIGS. 3N-P, downregulation of the mtp/apoB pathway results in a significant decrease in the levels of the yfp transcript. These results provide evidence for a mechanism involving transcriptional regulation of vegfr1 in response to apoB-lipoprotein levels. Whether this is a direct or indirect regulation still remains to be elucidated.

Example 4 apoB Particles Regulate Angiogenesis by Directly Acting on Endothelial Cells

The present inventors next characterized the mechanism by which apoB lipoproteins exert their effects on angiogenesis. Since the vascular phenotype of stl mutants is not trigged by global lipid starvation (See FIG. 2), it was hypothesized that deficits of lipoproteins, directly sensed by endothelial cells, exert a pro-angiogenic response in these mutants. To test this hypothesis, the present inventors first examined whether exogenously supplied LDL could suppress ectopic sprouting in stl mutants when applied intravascularly. Injection of DiI-labeled LDL into 2.5 dpf stl; mutants resulted in strong reduction in both the number and length of ectopic SIV sprouts (FIGS. 4A-C), suggesting that circulating lipoproteins have the ability to activate pro- or anti-angiogenic mechanisms in endothelial cells.

Figures 4H, 4I, 4J:
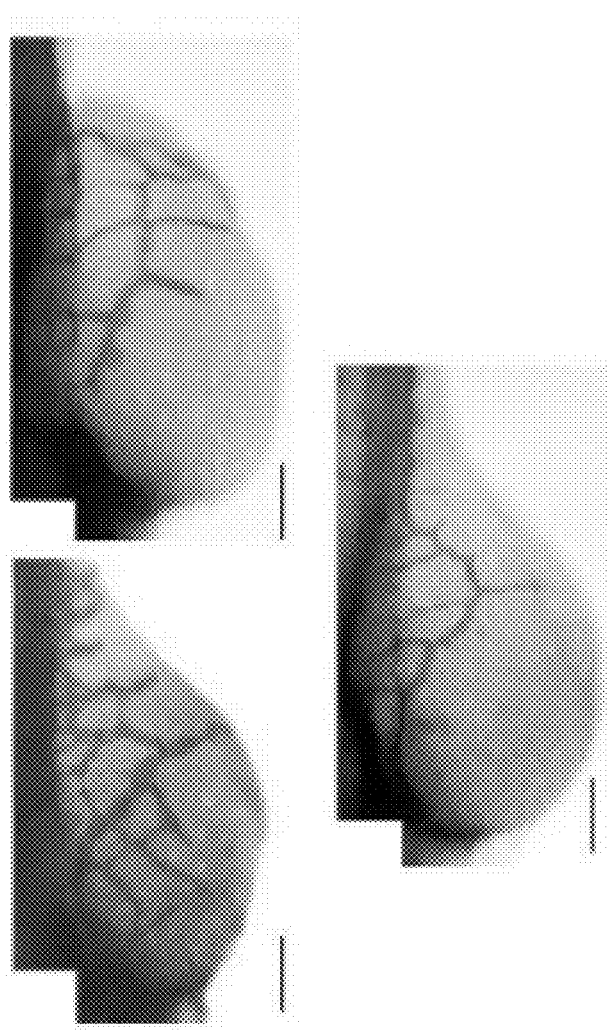
Figure 4G:
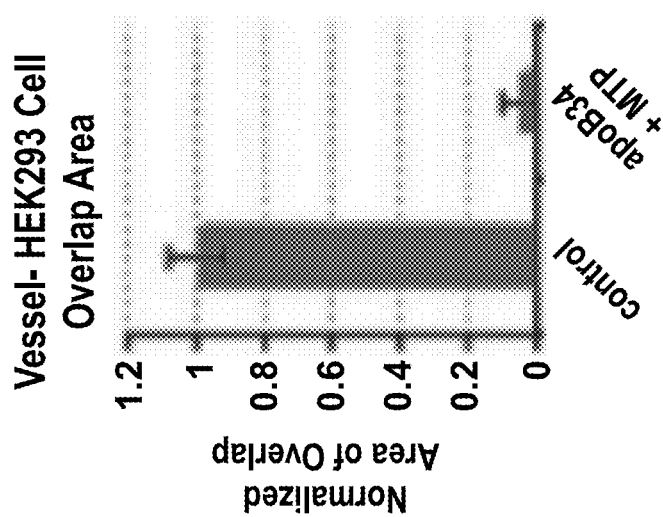

To further confirm the cell autonomous nature of the endothelial response the present inventors designed an in vivo approach to allow for localized delivery of exogenous apoB-particles in the proximity of angiogenic vessels (FIG. 4D). Lipoprotein-secreting HEK293 cells co-transfected with vectors encoding human forms of mtp and apoB34 (FIG. 14) or untransfected HEK293 control cells were transplanted into the perivitelline space, on one side of 2.5 dpf stl;Tg(fli-EGFP)$^{y1}$, animals, in close proximity to the forming SIVs (FIG. 4D). Lipoprotein-secreting cells impeded the migration of endothelial cells and the growth of ectopic sprouts in the area of transplantation (FIG. 4E, left panel). Ectopic SW sprouting however, was not affected on the untransplanted side of the same embryo (FIG. 4E, right panel), confirming that the localized transplantation did not result in systemic rescue of the stl phenotype. Non-lipoprotein-secreting cells, in contrast, did not impede sprouting or act as a barrier to endothelial migration (FIG. 4F). Quantitative analysis revealed a large decrease in endothelial migration onto lipoprotein-producing versus non-lipoprotein producing cells (FIG. 4G and FIG. 15). A similar direct inhibitory effect of LDL on endothelial cell migration was also observed in vitro (FIG. 16). The ability of ECs to migrate in Boyden chamber (FIG. 16A) and wound healing (FIG. 16B) assays was significantly impaired in LDL-supplemented media, even at concentration that did not affect cell proliferation (FIG. 16C). It is important to note however, that LDL levels considered pathological in human patients (>160 mg/dL), indeed result in endothelial cell death ($^{32}$ and data not shown). Together the in vivo and in vitro results indicate that endothelial cells respond cell-autonomously to changes in apoB-lipoprotein levels. This ability is not restricted to their luminal surface, yet, it seems to require direct contact, as xenografts that were not placed in close proximity to the developing vessels, did not result in any inhibitory effect (data not shown).

Finally the present inventors asked which component—the lipid moieties or the apoB protein itself—within apoB-lipoproteins plays a role in eliciting an endothelial response. To answer this question the present inventors took advantage of the fact that stl mutants lack secreted apoB-lipoproteins, and attempted to rescue their vascular phenotype by restoring different elements of the complex (lipid vs. protein) individually. While intravascular supply of free fatty acids (FIG. 4H, I, K) did not rescue the ectopic branching phenotype of stl mutants, injection of a delipidated form of apoB-100, significantly reduced the number and length of ectopic angiogenic sprouts (FIG. 4H, J, K). These results strongly support the idea that the apoB protein itself, and not the individual lipid elements within apoB-lipoproteins, act on endothelial cells to directly regulate angiogenesis.

Figure 4L:
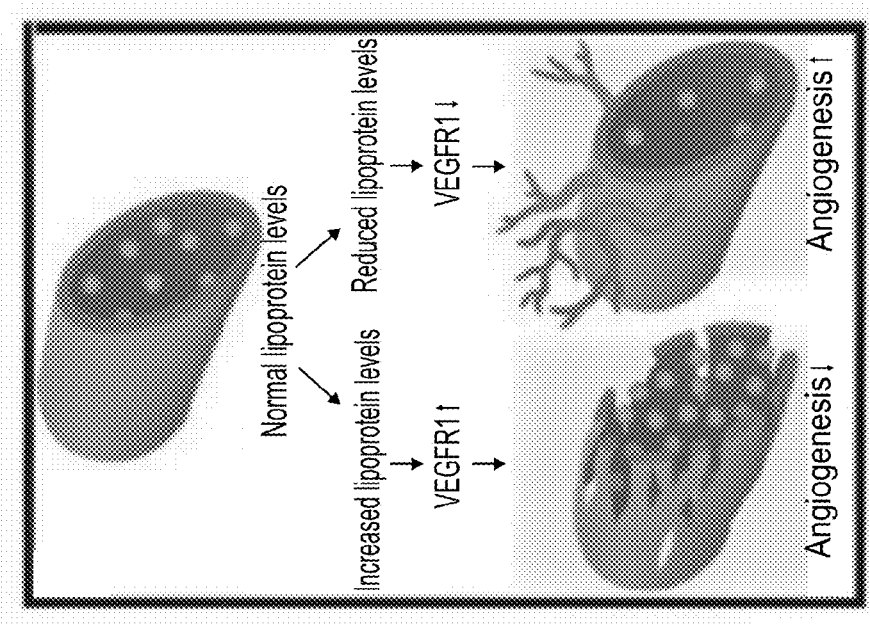
Figure 4K:
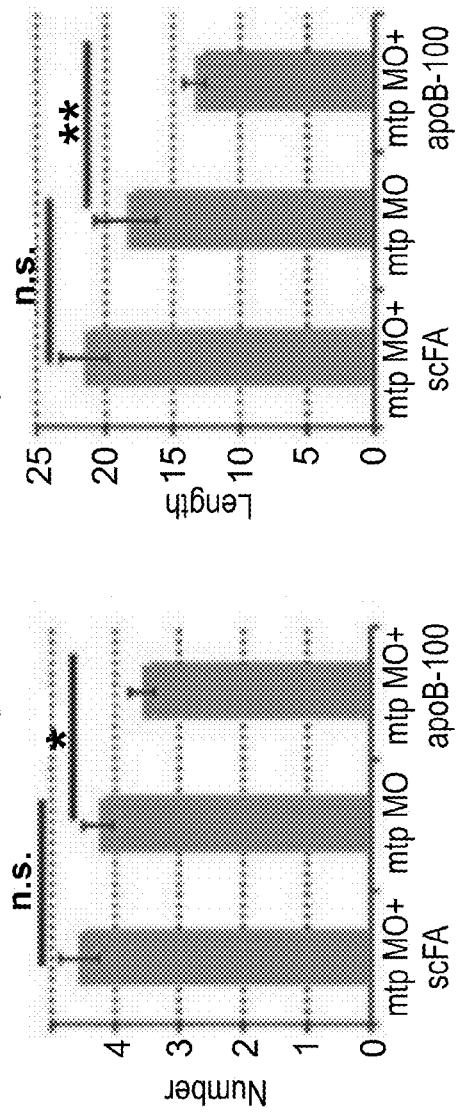

Endothelial-lipoprotein interactions have direct relevance to atherogenesis, thrombosis and other cardiovascular diseases. The results presented here reveal for the first time an intrinsic capacity of apoB-lipoproteins to control vascular growth in vivo, by regulating vegfr1 expression in endothelial cells (FIG. 4L).

Previous data hinted at direct interactions between the LDL and VEGF receptor families in vitro [Usui, R., EMBO Rep 8, 1155-1161 (2007); Yla-Herttuala, S. & Alitalo, K. EMBO Rep 8, 1127-1128 (2007), but the molecular mechanisms regulating this interplay remained obscure. The present examples show that VEGFR1 expression is regulated in vivo, by apoB-lipoprotein availability. Moreover it has been demonstrated that this regulation is mostly achieved at the transcriptional level.

Recent evidence suggests a potentially important role for the nutritional state of tissues in vessel growth. Taking advantage of the presently disclosed novel zebrafish models of hypo-, and hyperlipidemia, it has been possible to show that the effects of apoB-lipoproteins on angiogenesis are not trigged by reduced delivery of FA to tissues or global lipid starvation, as apoCII deficiency in zebrafish embryos did not phenocopy the vascular phenotype resulting from the loss of MTP. Further, the high plasma concentrations of TG-rich apoB-lipoproteins under these conditions inhibited angiogenesis, as did exogenous delivery of LDL. This effect however, required the presence of apoB, as intravascular supply of free FA did not affect vessel formation. Further supporting these findings, a delipidated form of apoB-100 efficiently reverted the excess angiogenesis phenotype of stl mutants, when applied intravascularly. These results support the notion that apoB itself provides the critical signal.

Several pathological conditions involve severe alterations in lipoprotein levels that result in a wide variety of vascular related diseases. These results have uncovered a novel mechanism of regulation of developmental angiogenesis by apoB-particles, which seems to be reactivated during pathological conditions of hyperlipidemia. These findings may provide novel explanations for endothelial dysfunction preceding the formation of atherogenic plaques, as well as for the impaired collateral vessel growth observed in hypercholesterolemic patients. Furthermore, these findings raise important questions about the potential effects of circulating lipoproteins during tumor-related angiogenesis.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating cancer in a subject in need thereof, the method comprising administering to the subject a therapeutically effective amount of a recombinant apolipoprotein B (ApoB) polypeptide comprising SEQ ID NO: 34 and capable of transcriptionally upregulating VEGFR1-, thereby treating the cancer.

2. The method of claim 1, wherein said cancer is a metastatic cancer.

3. The method of claim 1, wherein said administering is effected in vivo.

* * * * *

SEQUENCE LISTING

```
<160> NUMBER OF SEQ ID NOS: 34

<210> SEQ ID NO 1
<211> LENGTH: 25
<212> TYPE: DNA
<213> ORGANISM: Artificial sequence
<220> FEATURE:
<223> OTHER INFORMATION: Morpholino oligonucleotide

<400> SEQUENCE: 1
atatcgaaca ttctcttggt cttgc                                          25

<210> SEQ ID NO 2
<211> LENGTH: 25
<212> TYPE: DNA
<213> ORGANISM: Artificial sequence
<220> FEATURE:
<223> OTHER INFORMATION: Morpholino oligonucleotide

<400> SEQUENCE: 2
caacttagtg tccattttta tcggc                                          25

<210> SEQ ID NO 3
<211> LENGTH: 25
<212> TYPE: DNA
<213> ORGANISM: Artificial sequence
<220> FEATURE:
<223> OTHER INFORMATION: Morpholino oligonucleotide

<400> SEQUENCE: 3
tcagtgcaag agccacgaat ttcat                                          25

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
atgatgccgg ttgccggact                                                20

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
ttaccaggcc ggctcaaaga                                                20

<210> SEQ ID NO 6
<211> LENGTH: 31
<212> TYPE: DNA
<213> ORGANISM: Artificial sequence
```

```
<220> FEATURE:
<223> OTHER INFORMATION: Single strand DNA oligonucleotide

<400> SEQUENCE: 6
gaccaagaga atgttcgata tattatttgt g                              31

<210> SEQ ID NO 7
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 7
ttagaaactg gggtaaagaa gatcgccttc                                30

<210> SEQ ID NO 8
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 8
agaaagcttg ctggtcaata tgattcttct tgc                            33

<210> SEQ ID NO 9
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 9
agatctagaa tcacaggtca gtttcaaaac catcc                          35

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
ggcccgggat atttataaga ac                                        22

<210> SEQ ID NO 11
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 11
ccatccattt tagggggaagt c                                         21

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
gtctcgatcc cagtagacgg                                           20
```

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
tggtgcttgt ctcactgacc                                              20

<210> SEQ ID NO 14
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 14
tggtcatatg gagtcctgct c                                            21

<210> SEQ ID NO 15
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 15
catgttgagt cctgggtatg g                                            21

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
ctggtggaga ggctaggaga                                              20

<210> SEQ ID NO 17
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 17
tgatcgggat gtagtgcttt c                                            21

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
taaccaaccc ctccatcaga                                              20

<210> SEQ ID NO 19
<211> LENGTH: 21
<212> TYPE: DNA
<213> ORGANISM: Artificial sequence
<220> FEATURE:
<223> OTHER INFORMATION: Single strand DNA oligonucleotide

```
<400> SEQUENCE: 19
ctgaatgctg agagtccgat t                                              21

<210> SEQ ID NO 20
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 20
gcacatgaag atgtgttgaa tg                                             22

<210> SEQ ID NO 21
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 21
tggttagttc tggtgcattg tc                                             22

<210> SEQ ID NO 22
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 22
ccatctcacg gctgaccagt                                                20

<210> SEQ ID NO 23
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 23
gacagcgcac acaaccac                                                  18

<210> SEQ ID NO 24
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 24
cacatgaagc agcacgactt                                                20

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
ggtcttgtag ttgccgtcgt                                                20

<210> SEQ ID NO 26
```

```
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 26
cctctttctg ttacctggca aa                                              22

<210> SEQ ID NO 27
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 27 cttttcctttt cccatgattg a                                              21

<210> SEQ ID NO 28
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 28
tgacaggatg cagaaggaga                                                 20

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29
gcctccgatc cagacagagt                                                 20

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30
ccgtcttaca tggaggtgaa                                                 20

<210> SEQ ID NO 31
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 31
cggacatgga gaacatcttg                                                 20

<210> SEQ ID NO 32
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 32
```

```
cagctagtgc gaatatcatc t                                          21
```

<210> SEQ ID NO 33
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 33

```
tttctgtccc ataccaacc                                             19
```

<210> SEQ ID NO 34
<211> LENGTH: 4563
<212> TYPE: PRT
<213> ORGANISM: Homo sapiens

<400> SEQUENCE: 34

```
Met Asp Pro Pro Arg Pro Ala Leu Leu Ala Leu Leu Ala Leu Pro Ala
 1               5                  10                  15

Leu Leu Leu Leu Leu Leu Ala Gly Ala Arg Ala Glu Glu Glu Met Leu
                20                  25                  30

Glu Asn Val Ser Leu Val Cys Pro Lys Asp Ala Thr Arg Phe Lys His
            35                  40                  45

Leu Arg Lys Tyr Thr Tyr Asn Tyr Glu Ala Glu Ser Ser Ser Gly Val
    50                  55                  60

Pro Gly Thr Ala Asp Ser Arg Ser Ala Thr Arg Ile Asn Cys Lys Val
65                  70                  75                  80

Glu Leu Glu Val Pro Gln Leu Cys Ser Phe Ile Leu Lys Thr Ser Gln
                85                  90                  95

Cys Thr Leu Lys Glu Val Tyr Gly Phe Asn Pro Glu Gly Lys Ala Leu
            100                 105                 110

Leu Lys Lys Thr Lys Asn Ser Glu Glu Phe Ala Ala Ala Met Ser Arg
    115                 120                 125

Tyr Glu Leu Lys Leu Ala Ile Pro Glu Gly Lys Gln Val Phe Leu Tyr
    130                 135                 140

Pro Glu Lys Asp Glu Pro Thr Tyr Ile Leu Asn Ile Lys Arg Gly Ile
145                 150                 155                 160

Ile Ser Ala Leu Leu Val Pro Pro Glu Thr Glu Glu Ala Lys Gln Val
                165                 170                 175

Leu Phe Leu Asp Thr Val Tyr Gly Asn Cys Ser Thr His Phe Thr Val
            180                 185                 190

Lys Thr Arg Lys Gly Asn Val Ala Thr Glu Ile Ser Thr Glu Arg Asp
    195                 200                 205

Leu Gly Gln Cys Asp Arg Phe Lys Pro Ile Arg Thr Gly Ile Ser Pro
    210                 215                 220

Leu Ala Leu Ile Lys Gly Met Thr Arg Pro Leu Ser Thr Leu Ile Ser
225                 230                 235                 240

Ser Ser Gln Ser Cys Gln Tyr Thr Leu Asp Ala Lys Arg Lys His Val
                245                 250                 255

Ala Glu Ala Ile Cys Lys Glu Gln His Leu Phe Leu Pro Phe Ser Tyr
            260                 265                 270

Lys Asn Lys Tyr Gly Met Val Ala Gln Val Thr Gln Thr Leu Lys Leu
    275                 280                 285

Glu Asp Thr Pro Lys Ile Asn Ser Arg Phe Phe Gly Glu Gly Thr Lys
    290                 295                 300
```

-continued

```
Lys Met Gly Leu Ala Phe Glu Ser Thr Lys Ser Thr Ser Pro Pro Lys
305                 310                 315                 320

Gln Ala Glu Ala Val Leu Lys Thr Leu Gln Glu Leu Lys Lys Leu Thr
            325                 330                 335

Ile Ser Glu Gln Asn Ile Gln Arg Ala Asn Leu Phe Asn Lys Leu Val
        340                 345                 350

Thr Glu Leu Arg Gly Leu Ser Asp Glu Ala Val Thr Ser Leu Leu Pro
    355                 360                 365

Gln Leu Ile Glu Val Ser Ser Pro Ile Thr Leu Gln Ala Leu Val Gln
370                 375                 380

Cys Gly Gln Pro Gln Cys Ser Thr His Ile Leu Gln Trp Leu Lys Arg
385                 390                 395                 400

Val His Ala Asn Pro Leu Leu Ile Asp Val Val Thr Tyr Leu Val Ala
                405                 410                 415

Leu Ile Pro Glu Pro Ser Ala Gln Gln Leu Arg Glu Ile Phe Asn Met
            420                 425                 430

Ala Arg Asp Gln Arg Ser Arg Ala Thr Leu Tyr Ala Leu Ser His Ala
        435                 440                 445

Val Asn Asn Tyr His Lys Thr Asn Pro Thr Gly Thr Gln Glu Leu Leu
450                 455                 460

Asp Ile Ala Asn Tyr Leu Met Glu Gln Ile Gln Asp Asp Cys Thr Gly
465                 470                 475                 480

Asp Glu Asp Tyr Thr Tyr Leu Ile Leu Arg Val Ile Gly Asn Met Gly
                485                 490                 495

Gln Thr Met Glu Gln Leu Thr Pro Glu Leu Lys Ser Ser Ile Leu Lys
            500                 505                 510

Cys Val Gln Ser Thr Lys Pro Ser Leu Met Ile Gln Lys Ala Ala Ile
        515                 520                 525

Gln Ala Leu Arg Lys Met Glu Pro Lys Asp Lys Asp Gln Glu Val Leu
    530                 535                 540

Leu Gln Thr Phe Leu Asp Asp Ala Ser Pro Gly Asp Lys Arg Leu Ala
545                 550                 555                 560

Ala Tyr Leu Met Leu Met Arg Ser Pro Ser Gln Ala Asp Ile Asn Lys
                565                 570                 575

Ile Val Gln Ile Leu Pro Trp Glu Gln Asn Glu Gln Val Lys Asn Phe
            580                 585                 590

Val Ala Ser His Ile Ala Asn Ile Leu Asn Ser Glu Glu Leu Asp Ile
        595                 600                 605

Gln Asp Leu Lys Lys Leu Val Lys Glu Ala Leu Lys Glu Ser Gln Leu
    610                 615                 620

Pro Thr Val Met Asp Phe Arg Lys Phe Ser Arg Asn Tyr Gln Leu Tyr
625                 630                 635                 640

Lys Ser Val Ser Leu Pro Ser Leu Asp Pro Ala Ser Ala Lys Ile Glu
                645                 650                 655

Gly Asn Leu Ile Phe Asp Pro Asn Asn Tyr Leu Pro Lys Glu Ser Met
            660                 665                 670

Leu Lys Thr Thr Leu Thr Ala Phe Gly Phe Ala Ser Ala Asp Leu Ile
        675                 680                 685

Glu Ile Gly Leu Glu Gly Lys Gly Phe Glu Pro Thr Leu Glu Ala Leu
    690                 695                 700

Phe Gly Lys Gln Gly Phe Phe Pro Asp Ser Val Asn Lys Ala Leu Tyr
705                 710                 715                 720
```

```
Trp Val Asn Gly Gln Val Pro Asp Gly Val Ser Lys Val Leu Val Asp
            725                 730                 735

His Phe Gly Tyr Thr Lys Asp Asp Lys His Glu Gln Asp Met Val Asn
            740                 745                 750

Gly Ile Met Leu Ser Val Glu Lys Leu Ile Lys Asp Leu Lys Ser Lys
            755                 760                 765

Glu Val Pro Glu Ala Arg Ala Tyr Leu Arg Ile Leu Gly Glu Glu Leu
            770                 775                 780

Gly Phe Ala Ser Leu His Asp Leu Gln Leu Leu Gly Lys Leu Leu Leu
785                 790                 795                 800

Met Gly Ala Arg Thr Leu Gln Gly Ile Pro Gln Met Ile Gly Glu Val
                805                 810                 815

Ile Arg Lys Gly Ser Lys Asn Asp Phe Phe Leu His Tyr Ile Phe Met
            820                 825                 830

Glu Asn Ala Phe Glu Leu Pro Thr Gly Ala Gly Leu Gln Leu Gln Ile
            835                 840                 845

Ser Ser Ser Gly Val Ile Ala Pro Gly Ala Lys Ala Gly Val Lys Leu
850                 855                 860

Glu Val Ala Asn Met Gln Ala Glu Leu Val Ala Lys Pro Ser Val Ser
865                 870                 875                 880

Val Glu Phe Val Thr Asn Met Gly Ile Ile Pro Asp Phe Ala Arg
                885                 890                 895

Ser Gly Val Gln Met Asn Thr Asn Phe Phe His Glu Ser Gly Leu Glu
                900                 905                 910

Ala His Val Ala Leu Lys Ala Gly Lys Leu Lys Phe Ile Ile Pro Ser
            915                 920                 925

Pro Lys Arg Pro Val Lys Leu Leu Ser Gly Gly Asn Thr Leu His Leu
            930                 935                 940

Val Ser Thr Thr Lys Thr Glu Val Ile Pro Pro Leu Ile Glu Asn Arg
945                 950                 955                 960

Gln Ser Trp Ser Val Cys Lys Gln Val Phe Pro Gly Leu Asn Tyr Cys
                965                 970                 975

Thr Ser Gly Ala Tyr Ser Asn Ala Ser Ser Thr Asp Ser Ala Ser Tyr
            980                 985                 990

Tyr Pro Leu Thr Gly Asp Thr Arg Leu Glu Leu Glu Leu Arg Pro Thr
            995                 1000                1005

Gly Glu Ile Glu Gln Tyr Ser Val Ser Ala Thr Tyr Glu Leu Gln
    1010                1015                1020

Arg Glu Asp Arg Ala Leu Val Asp Thr Leu Lys Phe Val Thr Gln
    1025                1030                1035

Ala Glu Gly Ala Lys Gln Thr Glu Ala Thr Met Thr Phe Lys Tyr
    1040                1045                1050

Asn Arg Gln Ser Met Thr Leu Ser Ser Glu Val Gln Ile Pro Asp
    1055                1060                1065

Phe Asp Val Asp Leu Gly Thr Ile Leu Arg Val Asn Asp Glu Ser
    1070                1075                1080

Thr Glu Gly Lys Thr Ser Tyr Arg Leu Thr Leu Asp Ile Gln Asn
    1085                1090                1095

Lys Lys Ile Thr Glu Val Ala Leu Met Gly His Leu Ser Cys Asp
    1100                1105                1110

Thr Lys Glu Glu Arg Lys Ile Lys Gly Val Ile Ser Ile Pro Arg
    1115                1120                1125

Leu Gln Ala Glu Ala Arg Ser Glu Ile Leu Ala His Trp Ser Pro
```

```
                   1130               1135               1140

Ala Lys Leu Leu Leu Gln Met Asp Ser Ser Ala Thr Ala Tyr Gly
        1145                1150                1155

Ser Thr Val Ser Lys Arg Val Ala Trp His Tyr Asp Glu Glu Lys
        1160                1165                1170

Ile Glu Phe Glu Trp Asn Thr Gly Thr Asn Val Asp Thr Lys Lys
        1175                1180                1185

Met Thr Ser Asn Phe Pro Val Asp Leu Ser Asp Tyr Pro Lys Ser
        1190                1195                1200

Leu His Met Tyr Ala Asn Arg Leu Leu Asp His Arg Val Pro Gln
        1205                1210                1215

Thr Asp Met Thr Phe Arg His Val Gly Ser Lys Leu Ile Val Ala
        1220                1225                1230

Met Ser Ser Trp Leu Gln Lys Ala Ser Gly Ser Leu Pro Tyr Thr
        1235                1240                1245

Gln Thr Leu Gln Asp His Leu Asn Ser Leu Lys Glu Phe Asn Leu
        1250                1255                1260

Gln Asn Met Gly Leu Pro Asp Phe His Ile Pro Glu Asn Leu Phe
        1265                1270                1275

Leu Lys Ser Asp Gly Arg Val Lys Tyr Thr Leu Asn Lys Asn Ser
        1280                1285                1290

Leu Lys Ile Glu Ile Pro Leu Pro Phe Gly Gly Lys Ser Ser Arg
        1295                1300                1305

Asp Leu Lys Met Leu Glu Thr Val Arg Thr Pro Ala Leu His Phe
        1310                1315                1320

Lys Ser Val Gly Phe His Leu Pro Ser Arg Glu Phe Gln Val Pro
        1325                1330                1335

Thr Phe Thr Ile Pro Lys Leu Tyr Gln Leu Gln Val Pro Leu Leu
        1340                1345                1350

Gly Val Leu Asp Leu Ser Thr Asn Val Tyr Ser Asn Leu Tyr Asn
        1355                1360                1365

Trp Ser Ala Ser Tyr Ser Gly Gly Asn Thr Ser Thr Asp His Phe
        1370                1375                1380

Ser Leu Arg Ala Arg Tyr His Met Lys Ala Asp Ser Val Val Asp
        1385                1390                1395

Leu Leu Ser Tyr Asn Val Gln Gly Ser Gly Glu Thr Thr Tyr Asp
        1400                1405                1410

His Lys Asn Thr Phe Thr Leu Ser Tyr Asp Gly Ser Leu Arg His
        1415                1420                1425

Lys Phe Leu Asp Ser Asn Ile Lys Phe Ser His Val Glu Lys Leu
        1430                1435                1440

Gly Asn Asn Pro Val Ser Lys Gly Leu Leu Ile Phe Asp Ala Ser
        1445                1450                1455

Ser Ser Trp Gly Pro Gln Met Ser Ala Ser Val His Leu Asp Ser
        1460                1465                1470

Lys Lys Lys Gln His Leu Phe Val Lys Glu Val Lys Ile Asp Gly
        1475                1480                1485

Gln Phe Arg Val Ser Ser Phe Tyr Ala Lys Gly Thr Tyr Gly Leu
        1490                1495                1500

Ser Cys Gln Arg Asp Pro Asn Thr Gly Arg Leu Asn Gly Glu Ser
        1505                1510                1515

Asn Leu Arg Phe Asn Ser Ser Tyr Leu Gln Gly Thr Asn Gln Ile
        1520                1525                1530
```

```
Thr Gly Arg Tyr Glu Asp Gly Thr Leu Ser Leu Thr Ser Thr Ser
    1535                1540                1545

Asp Leu Gln Ser Gly Ile Ile Lys Asn Thr Ala Ser Leu Lys Tyr
    1550                1555                1560

Glu Asn Tyr Glu Leu Thr Leu Lys Ser Asp Thr Asn Gly Lys Tyr
    1565                1570                1575

Lys Asn Phe Ala Thr Ser Asn Lys Met Asp Met Thr Phe Ser Lys
    1580                1585                1590

Gln Asn Ala Leu Leu Arg Ser Glu Tyr Gln Ala Asp Tyr Glu Ser
    1595                1600                1605

Leu Arg Phe Phe Ser Leu Leu Ser Gly Ser Leu Asn Ser His Gly
    1610                1615                1620

Leu Glu Leu Asn Ala Asp Ile Leu Gly Thr Asp Lys Ile Asn Ser
    1625                1630                1635

Gly Ala His Lys Ala Thr Leu Arg Ile Gly Gln Asp Gly Ile Ser
    1640                1645                1650

Thr Ser Ala Thr Thr Asn Leu Lys Cys Ser Leu Leu Val Leu Glu
    1655                1660                1665

Asn Glu Leu Asn Ala Glu Leu Gly Leu Ser Gly Ala Ser Met Lys
    1670                1675                1680

Leu Thr Thr Asn Gly Arg Phe Arg Glu His Asn Ala Lys Phe Ser
    1685                1690                1695

Leu Asp Gly Lys Ala Ala Leu Thr Glu Leu Ser Leu Gly Ser Ala
    1700                1705                1710

Tyr Gln Ala Met Ile Leu Gly Val Asp Ser Lys Asn Ile Phe Asn
    1715                1720                1725

Phe Lys Val Ser Gln Glu Gly Leu Lys Leu Ser Asn Asp Met Met
    1730                1735                1740

Gly Ser Tyr Ala Glu Met Lys Phe Asp His Thr Asn Ser Leu Asn
    1745                1750                1755

Ile Ala Gly Leu Ser Leu Asp Phe Ser Ser Lys Leu Asp Asn Ile
    1760                1765                1770

Tyr Ser Ser Asp Lys Phe Tyr Lys Gln Thr Val Asn Leu Gln Leu
    1775                1780                1785

Gln Pro Tyr Ser Leu Val Thr Thr Leu Asn Ser Asp Leu Lys Tyr
    1790                1795                1800

Asn Ala Leu Asp Leu Thr Asn Asn Gly Lys Leu Arg Leu Glu Pro
    1805                1810                1815

Leu Lys Leu His Val Ala Gly Asn Leu Lys Gly Ala Tyr Gln Asn
    1820                1825                1830

Asn Glu Ile Lys His Ile Tyr Ala Ile Ser Ser Ala Ala Leu Ser
    1835                1840                1845

Ala Ser Tyr Lys Ala Asp Thr Val Ala Lys Val Gln Gly Val Glu
    1850                1855                1860

Phe Ser His Arg Leu Asn Thr Asp Ile Ala Gly Leu Ala Ser Ala
    1865                1870                1875

Ile Asp Met Ser Thr Asn Tyr Asn Ser Asp Ser Leu His Phe Ser
    1880                1885                1890

Asn Val Phe Arg Ser Val Met Ala Pro Phe Thr Met Thr Ile Asp
    1895                1900                1905

Ala His Thr Asn Gly Asn Gly Lys Leu Ala Leu Trp Gly Glu His
    1910                1915                1920
```

-continued

```
Thr Gly Gln Leu Tyr Ser Lys Phe Leu Leu Lys Ala Glu Pro Leu
1925                1930                1935

Ala Phe Thr Phe Ser His Asp Tyr Lys Gly Ser Thr Ser His His
1940                1945                1950

Leu Val Ser Arg Lys Ser Ile Ser Ala Ala Leu Glu His Lys Val
1955                1960                1965

Ser Ala Leu Leu Thr Pro Ala Glu Gln Thr Gly Thr Trp Lys Leu
1970                1975                1980

Lys Thr Gln Phe Asn Asn Asn Glu Tyr Ser Gln Asp Leu Asp Ala
1985                1990                1995

Tyr Asn Thr Lys Asp Lys Ile Gly Val Glu Leu Thr Gly Arg Thr
2000                2005                2010

Leu Ala Asp Leu Thr Leu Leu Asp Ser Pro Ile Lys Val Pro Leu
2015                2020                2025

Leu Leu Ser Glu Pro Ile Asn Ile Ile Asp Ala Leu Glu Met Arg
2030                2035                2040

Asp Ala Val Glu Lys Pro Gln Glu Phe Thr Ile Val Ala Phe Val
2045                2050                2055

Lys Tyr Asp Lys Asn Gln Asp Val His Ser Ile Asn Leu Pro Phe
2060                2065                2070

Phe Glu Thr Leu Gln Glu Tyr Phe Glu Arg Asn Arg Gln Thr Ile
2075                2080                2085

Ile Val Val Leu Glu Asn Val Gln Arg Asn Leu Lys His Ile Asn
2090                2095                2100

Ile Asp Gln Phe Val Arg Lys Tyr Arg Ala Ala Leu Gly Lys Leu
2105                2110                2115

Pro Gln Gln Ala Asn Asp Tyr Leu Asn Ser Phe Asn Trp Glu Arg
2120                2125                2130

Gln Val Ser His Ala Lys Glu Lys Leu Thr Ala Leu Thr Lys Lys
2135                2140                2145

Tyr Arg Ile Thr Glu Asn Asp Ile Gln Ile Ala Leu Asp Asp Ala
2150                2155                2160

Lys Ile Asn Phe Asn Glu Lys Leu Ser Gln Leu Gln Thr Tyr Met
2165                2170                2175

Ile Gln Phe Asp Gln Tyr Ile Lys Asp Ser Tyr Asp Leu His Asp
2180                2185                2190

Leu Lys Ile Ala Ile Ala Asn Ile Ile Asp Glu Ile Ile Glu Lys
2195                2200                2205

Leu Lys Ser Leu Asp Glu His Tyr His Ile Arg Val Asn Leu Val
2210                2215                2220

Lys Thr Ile His Asp Leu His Leu Phe Ile Glu Asn Ile Asp Phe
2225                2230                2235

Asn Lys Ser Gly Ser Ser Thr Ala Ser Trp Ile Gln Asn Val Asp
2240                2245                2250

Thr Lys Tyr Gln Ile Arg Ile Gln Ile Gln Glu Lys Leu Gln Gln
2255                2260                2265

Leu Lys Arg His Ile Gln Asn Ile Asp Ile Gln His Leu Ala Gly
2270                2275                2280

Lys Leu Lys Gln His Ile Glu Ala Ile Asp Val Arg Val Leu Leu
2285                2290                2295

Asp Gln Leu Gly Thr Thr Ile Ser Phe Glu Arg Ile Asn Asp Ile
2300                2305                2310

Leu Glu His Val Lys His Phe Val Ile Asn Leu Ile Gly Asp Phe
```

-continued

```
            2315                2320                2325
Glu Val Ala Glu Lys Ile Asn Ala Phe Arg Ala Lys Val His Glu
            2330                2335                2340
Leu Ile Glu Arg Tyr Glu Val Asp Gln Gln Ile Gln Val Leu Met
            2345                2350                2355
Asp Lys Leu Val Glu Leu Ala His Gln Tyr Lys Leu Lys Glu Thr
            2360                2365                2370
Ile Gln Lys Leu Ser Asn Val Leu Gln Gln Val Lys Ile Lys Asp
            2375                2380                2385
Tyr Phe Glu Lys Leu Val Gly Phe Ile Asp Asp Ala Val Lys Lys
            2390                2395                2400
Leu Asn Glu Leu Ser Phe Lys Thr Phe Ile Glu Asp Val Asn Lys
            2405                2410                2415
Phe Leu Asp Met Leu Ile Lys Lys Leu Lys Ser Phe Asp Tyr His
            2420                2425                2430
Gln Phe Val Asp Glu Thr Asn Asp Lys Ile Arg Glu Val Thr Gln
            2435                2440                2445
Arg Leu Asn Gly Glu Ile Gln Ala Leu Glu Leu Pro Gln Lys Ala
            2450                2455                2460
Glu Ala Leu Lys Leu Phe Leu Glu Glu Thr Lys Ala Thr Val Ala
            2465                2470                2475
Val Tyr Leu Glu Ser Leu Gln Asp Thr Lys Ile Thr Leu Ile Ile
            2480                2485                2490
Asn Trp Leu Gln Glu Ala Leu Ser Ser Ala Ser Leu Ala His Met
            2495                2500                2505
Lys Ala Lys Phe Arg Glu Thr Leu Glu Asp Thr Arg Asp Arg Met
            2510                2515                2520
Tyr Gln Met Asp Ile Gln Gln Glu Leu Gln Arg Tyr Leu Ser Leu
            2525                2530                2535
Val Gly Gln Val Tyr Ser Thr Leu Val Thr Tyr Ile Ser Asp Trp
            2540                2545                2550
Trp Thr Leu Ala Ala Lys Asn Leu Thr Asp Phe Ala Glu Gln Tyr
            2555                2560                2565
Ser Ile Gln Asp Trp Ala Lys Arg Met Lys Ala Leu Val Glu Gln
            2570                2575                2580
Gly Phe Thr Val Pro Glu Ile Lys Thr Ile Leu Gly Thr Met Pro
            2585                2590                2595
Ala Phe Glu Val Ser Leu Gln Ala Leu Gln Lys Ala Thr Phe Gln
            2600                2605                2610
Thr Pro Asp Phe Ile Val Pro Leu Thr Asp Leu Arg Ile Pro Ser
            2615                2620                2625
Val Gln Ile Asn Phe Lys Asp Leu Lys Asn Ile Lys Ile Pro Ser
            2630                2635                2640
Arg Phe Ser Thr Pro Glu Phe Thr Ile Leu Asn Thr Phe His Ile
            2645                2650                2655
Pro Ser Phe Thr Ile Asp Phe Val Glu Met Lys Val Lys Ile Ile
            2660                2665                2670
Arg Thr Ile Asp Gln Met Leu Asn Ser Glu Leu Gln Trp Pro Val
            2675                2680                2685
Pro Asp Ile Tyr Leu Arg Asp Leu Lys Val Glu Asp Ile Pro Leu
            2690                2695                2700
Ala Arg Ile Thr Leu Pro Asp Phe Arg Leu Pro Glu Ile Ala Ile
            2705                2710                2715
```

-continued

Pro Glu Phe Ile Ile Pro Thr Leu Asn Leu Asn Asp Phe Gln Val
2720                2725                2730

Pro Asp Leu His Ile Pro Glu Phe Gln Leu Pro His Ile Ser His
2735                2740                2745

Thr Ile Glu Val Pro Thr Phe Gly Lys Leu Tyr Ser Ile Leu Lys
2750                2755                2760

Ile Gln Ser Pro Leu Phe Thr Leu Asp Ala Asn Ala Asp Ile Gly
2765                2770                2775

Asn Gly Thr Thr Ser Ala Asn Glu Ala Gly Ile Ala Ala Ser Ile
2780                2785                2790

Thr Ala Lys Gly Glu Ser Lys Leu Glu Val Leu Asn Phe Asp Phe
2795                2800                2805

Gln Ala Asn Ala Gln Leu Ser Asn Pro Lys Ile Asn Pro Leu Ala
2810                2815                2820

Leu Lys Glu Ser Val Lys Phe Ser Ser Lys Tyr Leu Arg Thr Glu
2825                2830                2835

His Gly Ser Glu Met Leu Phe Phe Gly Asn Ala Ile Glu Gly Lys
2840                2845                2850

Ser Asn Thr Val Ala Ser Leu His Thr Glu Lys Asn Thr Leu Glu
2855                2860                2865

Leu Ser Asn Gly Val Ile Val Lys Ile Asn Asn Gln Leu Thr Leu
2870                2875                2880

Asp Ser Asn Thr Lys Tyr Phe His Lys Leu Asn Ile Pro Lys Leu
2885                2890                2895

Asp Phe Ser Ser Gln Ala Asp Leu Arg Asn Glu Ile Lys Thr Leu
2900                2905                2910

Leu Lys Ala Gly His Ile Ala Trp Thr Ser Ser Gly Lys Gly Ser
2915                2920                2925

Trp Lys Trp Ala Cys Pro Arg Phe Ser Asp Glu Gly Thr His Glu
2930                2935                2940

Ser Gln Ile Ser Phe Thr Ile Glu Gly Pro Leu Thr Ser Phe Gly
2945                2950                2955

Leu Ser Asn Lys Ile Asn Ser Lys His Leu Arg Val Asn Gln Asn
2960                2965                2970

Leu Val Tyr Glu Ser Gly Ser Leu Asn Phe Ser Lys Leu Glu Ile
2975                2980                2985

Gln Ser Gln Val Asp Ser Gln His Val Gly His Ser Val Leu Thr
2990                2995                3000

Ala Lys Gly Met Ala Leu Phe Gly Glu Gly Lys Ala Glu Phe Thr
3005                3010                3015

Gly Arg His Asp Ala His Leu Asn Gly Lys Val Ile Gly Thr Leu
3020                3025                3030

Lys Asn Ser Leu Phe Phe Ser Ala Gln Pro Phe Glu Ile Thr Ala
3035                3040                3045

Ser Thr Asn Asn Glu Gly Asn Leu Lys Val Arg Phe Pro Leu Arg
3050                3055                3060

Leu Thr Gly Lys Ile Asp Phe Leu Asn Asn Tyr Ala Leu Phe Leu
3065                3070                3075

Ser Pro Ser Ala Gln Gln Ala Ser Trp Gln Val Ser Ala Arg Phe
3080                3085                3090

Asn Gln Tyr Lys Tyr Asn Gln Asn Phe Ser Ala Gly Asn Asn Glu
3095                3100                3105

-continued

```
Asn Ile Met Glu Ala His Val Gly Ile Asn Gly Glu Ala Asn Leu
3110                3115                3120

Asp Phe Leu Asn Ile Pro Leu Thr Ile Pro Glu Met Arg Leu Pro
3125                3130                3135

Tyr Thr Ile Ile Thr Thr Pro Pro Leu Lys Asp Phe Ser Leu Trp
3140                3145                3150

Glu Lys Thr Gly Leu Lys Glu Phe Leu Lys Thr Thr Lys Gln Ser
3155                3160                3165

Phe Asp Leu Ser Val Lys Ala Gln Tyr Lys Lys Asn Lys His Arg
3170                3175                3180

His Ser Ile Thr Asn Pro Leu Ala Val Leu Cys Glu Phe Ile Ser
3185                3190                3195

Gln Ser Ile Lys Ser Phe Asp Arg His Phe Glu Lys Asn Arg Asn
3200                3205                3210

Asn Ala Leu Asp Phe Val Thr Lys Ser Tyr Asn Glu Thr Lys Ile
3215                3220                3225

Lys Phe Asp Lys Tyr Lys Ala Glu Lys Ser His Asp Glu Leu Pro
3230                3235                3240

Arg Thr Phe Gln Ile Pro Gly Tyr Thr Val Pro Val Val Asn Val
3245                3250                3255

Glu Val Ser Pro Phe Thr Ile Glu Met Ser Ala Phe Gly Tyr Val
3260                3265                3270

Phe Pro Lys Ala Val Ser Met Pro Ser Phe Ser Ile Leu Gly Ser
3275                3280                3285

Asp Val Arg Val Pro Ser Tyr Thr Leu Ile Leu Pro Ser Leu Glu
3290                3295                3300

Leu Pro Val Leu His Val Pro Arg Asn Leu Lys Leu Ser Leu Pro
3305                3310                3315

Asp Phe Lys Glu Leu Cys Thr Ile Ser His Ile Phe Ile Pro Ala
3320                3325                3330

Met Gly Asn Ile Thr Tyr Asp Phe Ser Phe Lys Ser Ser Val Ile
3335                3340                3345

Thr Leu Asn Thr Asn Ala Glu Leu Phe Asn Gln Ser Asp Ile Val
3350                3355                3360

Ala His Leu Leu Ser Ser Ser Ser Ser Val Ile Asp Ala Leu Gln
3365                3370                3375

Tyr Lys Leu Glu Gly Thr Thr Arg Leu Thr Arg Lys Arg Gly Leu
3380                3385                3390

Lys Leu Ala Thr Ala Leu Ser Leu Ser Asn Lys Phe Val Glu Gly
3395                3400                3405

Ser His Asn Ser Thr Val Ser Leu Thr Thr Lys Asn Met Glu Val
3410                3415                3420

Ser Val Ala Thr Thr Thr Lys Ala Gln Ile Pro Ile Leu Arg Met
3425                3430                3435

Asn Phe Lys Gln Glu Leu Asn Gly Asn Thr Lys Ser Lys Pro Thr
3440                3445                3450

Val Ser Ser Ser Met Glu Phe Lys Tyr Asp Phe Asn Ser Ser Met
3455                3460                3465

Leu Tyr Ser Thr Ala Lys Gly Ala Val Asp His Lys Leu Ser Leu
3470                3475                3480

Glu Ser Leu Thr Ser Tyr Phe Ser Ile Glu Ser Ser Thr Lys Gly
3485                3490                3495

Asp Val Lys Gly Ser Val Leu Ser Arg Glu Tyr Ser Gly Thr Ile
```

-continued

```
              3500                3505                3510
Ala  Ser  Glu  Ala  Asn  Thr  Tyr  Leu  Asn  Ser  Lys  Ser  Thr  Arg  Ser
     3515                3520                3525

Ser  Val  Lys  Leu  Gln  Gly  Thr  Ser  Lys  Ile  Asp  Asp  Ile  Trp  Asn
     3530                3535                3540

Leu  Glu  Val  Lys  Glu  Asn  Phe  Ala  Gly  Glu  Ala  Thr  Leu  Gln  Arg
     3545                3550                3555

Ile  Tyr  Ser  Leu  Trp  Glu  His  Ser  Thr  Lys  Asn  His  Leu  Gln  Leu
     3560                3565                3570

Glu  Gly  Leu  Phe  Phe  Thr  Asn  Gly  Glu  His  Thr  Ser  Lys  Ala  Thr
     3575                3580                3585

Leu  Glu  Leu  Ser  Pro  Trp  Gln  Met  Ser  Ala  Leu  Val  Gln  Val  His
     3590                3595                3600

Ala  Ser  Gln  Pro  Ser  Ser  Phe  His  Asp  Phe  Pro  Asp  Leu  Gly  Gln
     3605                3610                3615

Glu  Val  Ala  Leu  Asn  Ala  Asn  Thr  Lys  Asn  Gln  Lys  Ile  Arg  Trp
     3620                3625                3630

Lys  Asn  Glu  Val  Arg  Ile  His  Ser  Gly  Ser  Phe  Gln  Ser  Gln  Val
     3635                3640                3645

Glu  Leu  Ser  Asn  Asp  Gln  Glu  Lys  Ala  His  Leu  Asp  Ile  Ala  Gly
     3650                3655                3660

Ser  Leu  Glu  Gly  His  Leu  Arg  Phe  Leu  Lys  Asn  Ile  Ile  Leu  Pro
     3665                3670                3675

Val  Tyr  Asp  Lys  Ser  Leu  Trp  Asp  Phe  Leu  Lys  Leu  Asp  Val  Thr
     3680                3685                3690

Thr  Ser  Ile  Gly  Arg  Arg  Gln  His  Leu  Arg  Val  Ser  Thr  Ala  Phe
     3695                3700                3705

Val  Tyr  Thr  Lys  Asn  Pro  Asn  Gly  Tyr  Ser  Phe  Ser  Ile  Pro  Val
     3710                3715                3720

Lys  Val  Leu  Ala  Asp  Lys  Phe  Ile  Ile  Pro  Gly  Leu  Lys  Leu  Asn
     3725                3730                3735

Asp  Leu  Asn  Ser  Val  Leu  Val  Met  Pro  Thr  Phe  His  Val  Pro  Phe
     3740                3745                3750

Thr  Asp  Leu  Gln  Val  Pro  Ser  Cys  Lys  Leu  Asp  Phe  Arg  Glu  Ile
     3755                3760                3765

Gln  Ile  Tyr  Lys  Lys  Leu  Arg  Thr  Ser  Ser  Phe  Ala  Leu  Asn  Leu
     3770                3775                3780

Pro  Thr  Leu  Pro  Glu  Val  Lys  Phe  Pro  Glu  Val  Asp  Val  Leu  Thr
     3785                3790                3795

Lys  Tyr  Ser  Gln  Pro  Glu  Asp  Ser  Leu  Ile  Pro  Phe  Phe  Glu  Ile
     3800                3805                3810

Thr  Val  Pro  Glu  Ser  Gln  Leu  Thr  Val  Ser  Gln  Phe  Thr  Leu  Pro
     3815                3820                3825

Lys  Ser  Val  Ser  Asp  Gly  Ile  Ala  Ala  Leu  Asp  Leu  Asn  Ala  Val
     3830                3835                3840

Ala  Asn  Lys  Ile  Ala  Asp  Phe  Glu  Leu  Pro  Thr  Ile  Ile  Val  Pro
     3845                3850                3855

Glu  Gln  Thr  Ile  Glu  Ile  Pro  Ser  Ile  Lys  Phe  Ser  Val  Pro  Ala
     3860                3865                3870

Gly  Ile  Val  Ile  Pro  Ser  Phe  Gln  Ala  Leu  Thr  Ala  Arg  Phe  Glu
     3875                3880                3885

Val  Asp  Ser  Pro  Val  Tyr  Asn  Ala  Thr  Trp  Ser  Ala  Ser  Leu  Lys
     3890                3895                3900
```

```
Asn Lys Ala Asp Tyr Val Glu Thr Val Leu Asp Ser Thr Cys Ser
    3905            3910            3915

Ser Thr Val Gln Phe Leu Glu Tyr Glu Leu Asn Val Leu Gly Thr
    3920            3925            3930

His Lys Ile Glu Asp Gly Thr Leu Ala Ser Lys Thr Lys Gly Thr
    3935            3940            3945

Phe Ala His Arg Asp Phe Ser Ala Glu Tyr Glu Glu Asp Gly Lys
    3950            3955            3960

Tyr Glu Gly Leu Gln Glu Trp Glu Gly Lys Ala His Leu Asn Ile
    3965            3970            3975

Lys Ser Pro Ala Phe Thr Asp Leu His Leu Arg Tyr Gln Lys Asp
    3980            3985            3990

Lys Lys Gly Ile Ser Thr Ser Ala Ala Ser Pro Ala Val Gly Thr
    3995            4000            4005

Val Gly Met Asp Met Asp Glu Asp Asp Phe Ser Lys Trp Asn
    4010            4015            4020

Phe Tyr Tyr Ser Pro Gln Ser Ser Pro Asp Lys Lys Leu Thr Ile
    4025            4030            4035

Phe Lys Thr Glu Leu Arg Val Arg Glu Ser Asp Glu Glu Thr Gln
    4040            4045            4050

Ile Lys Val Asn Trp Glu Glu Ala Ala Ser Gly Leu Leu Thr
    4055            4060            4065

Ser Leu Lys Asp Asn Val Pro Lys Ala Thr Gly Val Leu Tyr Asp
    4070            4075            4080

Tyr Val Asn Lys Tyr His Trp Glu His Thr Gly Leu Thr Leu Arg
    4085            4090            4095

Glu Val Ser Ser Lys Leu Arg Arg Asn Leu Gln Asn Asn Ala Glu
    4100            4105            4110

Trp Val Tyr Gln Gly Ala Ile Arg Gln Ile Asp Asp Ile Asp Val
    4115            4120            4125

Arg Phe Gln Lys Ala Ala Ser Gly Thr Thr Gly Thr Tyr Gln Glu
    4130            4135            4140

Trp Lys Asp Lys Ala Gln Asn Leu Tyr Gln Glu Leu Leu Thr Gln
    4145            4150            4155

Glu Gly Gln Ala Ser Phe Gln Gly Leu Lys Asp Asn Val Phe Asp
    4160            4165            4170

Gly Leu Val Arg Val Thr Gln Glu Phe His Met Lys Val Lys His
    4175            4180            4185

Leu Ile Asp Ser Leu Ile Asp Phe Leu Asn Phe Pro Arg Phe Gln
    4190            4195            4200

Phe Pro Gly Lys Pro Gly Ile Tyr Thr Arg Glu Glu Leu Cys Thr
    4205            4210            4215

Met Phe Ile Arg Glu Val Gly Thr Val Leu Ser Gln Val Tyr Ser
    4220            4225            4230

Lys Val His Asn Gly Ser Glu Ile Leu Phe Ser Tyr Phe Gln Asp
    4235            4240            4245

Leu Val Ile Thr Leu Pro Phe Glu Leu Arg Lys His Lys Leu Ile
    4250            4255            4260

Asp Val Ile Ser Met Tyr Arg Glu Leu Leu Lys Asp Leu Ser Lys
    4265            4270            4275

Glu Ala Gln Glu Val Phe Lys Ala Ile Gln Ser Leu Lys Thr Thr
    4280            4285            4290
```

```
Glu Val Leu Arg Asn Leu Gln Asp Leu Leu Gln Phe Ile Phe Gln
    4295            4300                4305
Leu Ile Glu Asp Asn Ile Lys Gln Leu Lys Glu Met Lys Phe Thr
    4310            4315                4320
Tyr Leu Ile Asn Tyr Ile Gln Asp Glu Ile Asn Thr Ile Phe Ser
    4325            4330                4335
Asp Tyr Ile Pro Tyr Val Phe Lys Leu Leu Lys Glu Asn Leu Cys
    4340            4345                4350
Leu Asn Leu His Lys Phe Asn Glu Phe Ile Gln Asn Glu Leu Gln
    4355            4360                4365
Glu Ala Ser Gln Glu Leu Gln Gln Ile His Gln Tyr Ile Met Ala
    4370            4375                4380
Leu Arg Glu Glu Tyr Phe Asp Pro Ser Ile Val Gly Trp Thr Val
    4385            4390                4395
Lys Tyr Tyr Glu Leu Glu Glu Lys Ile Val Ser Leu Ile Lys Asn
    4400            4405                4410
Leu Leu Val Ala Leu Lys Asp Phe His Ser Glu Tyr Ile Val Ser
    4415            4420                4425
Ala Ser Asn Phe Thr Ser Gln Leu Ser Ser Gln Val Glu Gln Phe
    4430            4435                4440
Leu His Arg Asn Ile Gln Glu Tyr Leu Ser Ile Leu Thr Asp Pro
    4445            4450                4455
Asp Gly Lys Gly Lys Glu Lys Ile Ala Glu Leu Ser Ala Thr Ala
    4460            4465                4470
Gln Glu Ile Ile Lys Ser Gln Ala Ile Ala Thr Lys Lys Ile Ile
    4475            4480                4485
Ser Asp Tyr His Gln Gln Phe Arg Tyr Lys Leu Gln Asp Phe Ser
    4490            4495                4500
Asp Gln Leu Ser Asp Tyr Tyr Glu Lys Phe Ile Ala Glu Ser Lys
    4505            4510                4515
Arg Leu Ile Asp Leu Ser Ile Gln Asn Tyr His Thr Phe Leu Ile
    4520            4525                4530
Tyr Ile Thr Glu Leu Leu Lys Lys Leu Gln Ser Thr Thr Val Met
    4535            4540                4545
Asn Pro Tyr Met Lys Leu Ala Pro Gly Glu Leu Thr Ile Ile Leu
    4550            4555                4560
```